(12) United States Patent
Barbe et al.

(10) Patent No.: US 12,340,890 B2
(45) Date of Patent: Jun. 24, 2025

(54) PEOPLE WELLNESS MONITORING

(71) Applicants: Brian Barbe, Haymarket, VA (US);
Alexander Wu, Haymarket, VA (US);
Seongyong Lim, Haymarket, VA (US);
Wesley Cheng, Haymarket, VA (US)

(72) Inventors: Brian Barbe, Haymarket, VA (US);
Alexander Wu, Haymarket, VA (US);
Seongyong Lim, Haymarket, VA (US);
Wesley Cheng, Haymarket, VA (US)

(73) Assignee: Stack Labs, Inc., Cupertino, CA (US)

( * ) Notice: Subject to any disclaimer, the term of this patent is extended or adjusted under 35 U.S.C. 154(b) by 289 days.

(21) Appl. No.: 18/201,630

(22) Filed: May 24, 2023

(65) Prior Publication Data
US 2024/0395386 A1 Nov. 28, 2024

(51) Int. Cl.
*G16H 20/30* (2018.01)
*A61B 5/00* (2006.01)
*G08B 21/04* (2006.01)
*G16H 20/70* (2018.01)
*G16H 40/67* (2018.01)

(52) U.S. Cl.
CPC .......... *G16H 20/30* (2018.01); *A61B 5/4815* (2013.01); *A61B 5/746* (2013.01); *G08B 21/0423* (2013.01); *G16H 20/70* (2018.01); *G16H 40/67* (2018.01)

(58) Field of Classification Search
None
See application file for complete search history.

(56) References Cited

U.S. PATENT DOCUMENTS 11,256,998 B2 * 2/2022 Mendels .................. G06N 5/04

* cited by examiner

*Primary Examiner* — K. Wong
(74) *Attorney, Agent, or Firm* — PatentPC; Bao Tran

(57) ABSTRACT

Systems and methods are disclosed for encouraging physical activity among one or more subjects by using sensors to track motion and other physical activity of the subject; creating an activity index based on the tracked data to measure overall activity levels; and providing feedback to the senior through a chatbot or other interface to encourage physical activity and suggest changes to their routines.

20 Claims, 32 Drawing Sheets

Temperature

Today, 3:37pm  
TYPICAL

75.3°F  
Average

Temperature is in the normal range.

TODAY

|  | | Current | Low | High |
|---|---|---|---|---|
| Bathroom | ——— | 74.8° | 63.6° | 74.8° |
| Bedroom | ——— | 71.1° | 61.0° | 71.1° |
| Kitchen | ——— | 80.0° | 62.7° | 80.0° |

RECENTLY          Last 3 Hours

Status

PEOPLE WELLNESS MONITORING

This application is related to copending application Ser. No. 18/201,648 entitled "Bandwidth and power-optimized hybrid high-resolution/low-resolution sensor method for a predictive analytics system", to copending application Ser. No. 18/201,618, 18201624, 18201628, 18201630 entitled "People Wellness Monitoring" and to copending application Ser. No. 18/201,637 entitled "Autonomous Circadian Lighting System with Environmental and Sensor Input", the content of which is incorporated by reference.

BACKGROUND

The present system relates to wellness monitoring.

The aging trend is a global phenomenon, and the world's population is rapidly getting older. According to the United Nations, the number of people aged 60 or above is projected to reach 1.4 billion by 2030 and 2.1 billion by 2050, which will account for 21% and 26% of the global population, respectively.

As people age, they may experience various physical and cognitive changes, which can increase their vulnerability to health risks, such as falls, chronic diseases, and cognitive decline. Monitoring the health and well-being of elderly individuals is crucial to ensure their safety and providing appropriate care.

Elderly monitoring can help to detect any changes in an individual's health status, such as a sudden increase in blood pressure, changes in bathroom visits, or a change in sleep patterns, that may require medical attention. Monitoring can also help to prevent falls by detecting any signs of mobility impairment or environmental hazards that may pose a risk.

Moreover, elderly monitoring can provide peace of mind for family members and caregivers who may not be able to physically check on the individual's well-being regularly. Remote monitoring systems, such as StackCare, offer a comprehensive solution for elderly monitoring, providing continuous tracking of vital signs, activity levels, and safety. They also allow caregivers to remotely monitor their loved ones' health status.

Overall, the aging trend highlights the need for elderly monitoring solutions that can ensure the safety and well-being of elderly individuals while also providing support for their caregivers and family members.

SUMMARY

Systems and methods are disclosed to monitor wellness of a person by capturing streaming data from one or more sensors; applying one or more deep learning models to identify one or more activities of the person; applying one or more directed acyclic graphs (DAGs) to the streaming data and the one or more activities of the person to identify a pattern from the streaming data for alert or notification of one or more predefined conditions affecting wellness; and generating one or more notifications or alerts to a caregiver or a family member to assist the person.

Other aspects can include one or more of the following.

A method for real-time stream processing of motion/contact/attribute data, including the steps of capturing user activity data through sensors, triggering notifications based on predetermined criteria, and implementing said method using Kafka brokers and Kubernetes.

A method for detecting motion activity and bathroom visits, including the steps of cleaning up motion data, processing zone occupancy, and calculating bathroom visits, and executing said method using SQL and BigQuery for scalability.

A method for notifying caregivers of relevant events, including the steps of setting inhibitions based on time since last event, implementing related events such as bathroom overstays, and using machine learning to determine sleep duration and quality.

A method for identifying actual and optimal go-to-bed time, including the steps of training a random forest model using identified sleep features and labeled data, and developing a classification algorithm for determining said actual or optimal time.

A method for calculating sleep duration with up & about time, including the steps of analyzing motion data, identifying periods of wakefulness, and determining sleep duration based on said data.

A method for calculating sleep quality using motion levels, including the steps of analyzing high, low, and no motion data, and using said analysis to determine sleep quality.

A method for detecting outliers in bathroom visit data, including the steps of continually updating said data for all users, counting only visits with possible toilet usage, and calculating a minimum duration per user based on nighttime usage.

A method for measuring temperature and humidity levels, including the steps of collecting temperature and humidity reports every 10-12 minutes, and calculating heat index based on said data.

A method for triggering temperature warning notifications, including the steps of setting high and low temperature thresholds, requiring two consecutive temperatures above or below said thresholds to trigger a notification, and sending said notification to relevant caregivers.

A method for triggering exit notifications, including the steps of requiring motion in a zone prior to door open, checking for motion 30 seconds after door close, and sending a notification if no motion is detected, and checking for motion 120 seconds after door open and sending a follow-up notification if said motion is detected.

Other aspects include the following systems and methods:

An environmental monitoring system, including: a plurality of sensors for measuring environmental factors; and a data processing unit for analyzing the measured data and generating alerts based on predefined criteria.

A motion processing apparatus, including: a motion sensor for detecting movement within a designated area; and a data processing unit for analyzing the motion data and generating notifications based on predefined criteria.

A temperature monitoring system, including: a temperature sensor for measuring ambient temperature; and a data processing unit for analyzing the temperature data and generating alerts based on predefined temperature thresholds.

A sleep monitoring device, including: a motion sensor for detecting body movement during sleep; a data processing unit for analyzing the motion data and calculating sleep duration and quality metrics.

A lighting control system, including: a plurality of sensors for measuring environmental factors; and a data processing unit for generating lighting plans based on the measured data and predefined criteria.

An exit monitoring device, including: a contact sensor for detecting the opening and closing of an exterior door; a motion sensor for detecting movement within a designated area; and a data processing unit for generating notifications based on predefined criteria.

A help button monitoring device, including: a help button for triggering an alert when pressed; a data processing unit for generating notifications based on the alert.

A security monitoring system, including: a plurality of motion sensors for detecting movement within designated areas; a data processing unit for analyzing the motion data and generating notifications based on predefined criteria.

A bathroom monitoring system, including: a motion sensor for detecting movement within a bathroom; a data processing unit for analyzing the motion data and generating notifications based on predefined criteria.

A humidity monitoring system, including: a humidity sensor for measuring ambient humidity; a data processing unit for analyzing the humidity data and generating alerts based on predefined humidity thresholds.

Advantages of the system may include one or more of the following. The system provides monitoring solutions for elderly individuals who are living independently or in assisted living facilities. The service utilizes a combination of wearable devices and sensors placed throughout the home to track the individual's activity levels, health metrics, and safety. The system can work with wearable devices such as a smartwatch or a pendant that tracks the individual's movements and vital signs, such as heart rate, blood pressure, and oxygen levels. The sensors placed throughout the home detect activity levels and alert caregivers or family members if abnormal behavior is detected, such as prolonged inactivity or a fall. The service also offers a mobile app that allows caregivers or family members remotely monitor the individual's activity levels and health metrics. The app can send notifications to alert caregivers or family members of any changes in the individual's behavior, such as a missed medication dose or a sudden change in activity levels. The system provides a comprehensive monitoring solution that allows elderly individuals to maintain their independence while also providing peace of mind for caregivers and family members. Yet further advantages of the system may include:

Real-time monitoring: The system is designed for real-time monitoring of various sensors and data streams, allowing for rapid detection of potential issues and immediate notification of relevant parties.

Customizable notifications: The system allows for customizable notifications based on specific criteria, allowing for tailored alerts to be sent to relevant parties.

Efficient data processing: The use of Kafka and Kubernetes for data processing and streamlining allows for efficient data processing and analysis.

Scalability: The use of SQL and BigQuery allows for scalability, making it possible to process data for a large number of sites.

Sleep analysis: The use of machine learning algorithms to analyze sleep data allows for personalized insights into sleep duration and quality.

Environmental control: The use of circadian lighting and other environmental factors can help promote a healthy living environment for residents.

Outlier detection: The use of outlier detection algorithms allows for identification of potentially problematic events, such as prolonged bathroom visits or excessive elder bad habits.

Monitoring of frequent activities such as cooking or bathroom visits: The monitoring of visits to the kitchen and or the bathroom helps to provide more accurate data on actual daily life.

Contextual lighting: The use of environmental factors to provide contextual lighting can help to reduce energy costs while still promoting health and well-being.

Improved safety: The use of real-time monitoring and customizable notifications can help improve safety for residents, alerting caregivers to potential issues such as exits and help requests.

BRIEF DESCRIPTION OF THE DRAWINGS

Figure 7K:
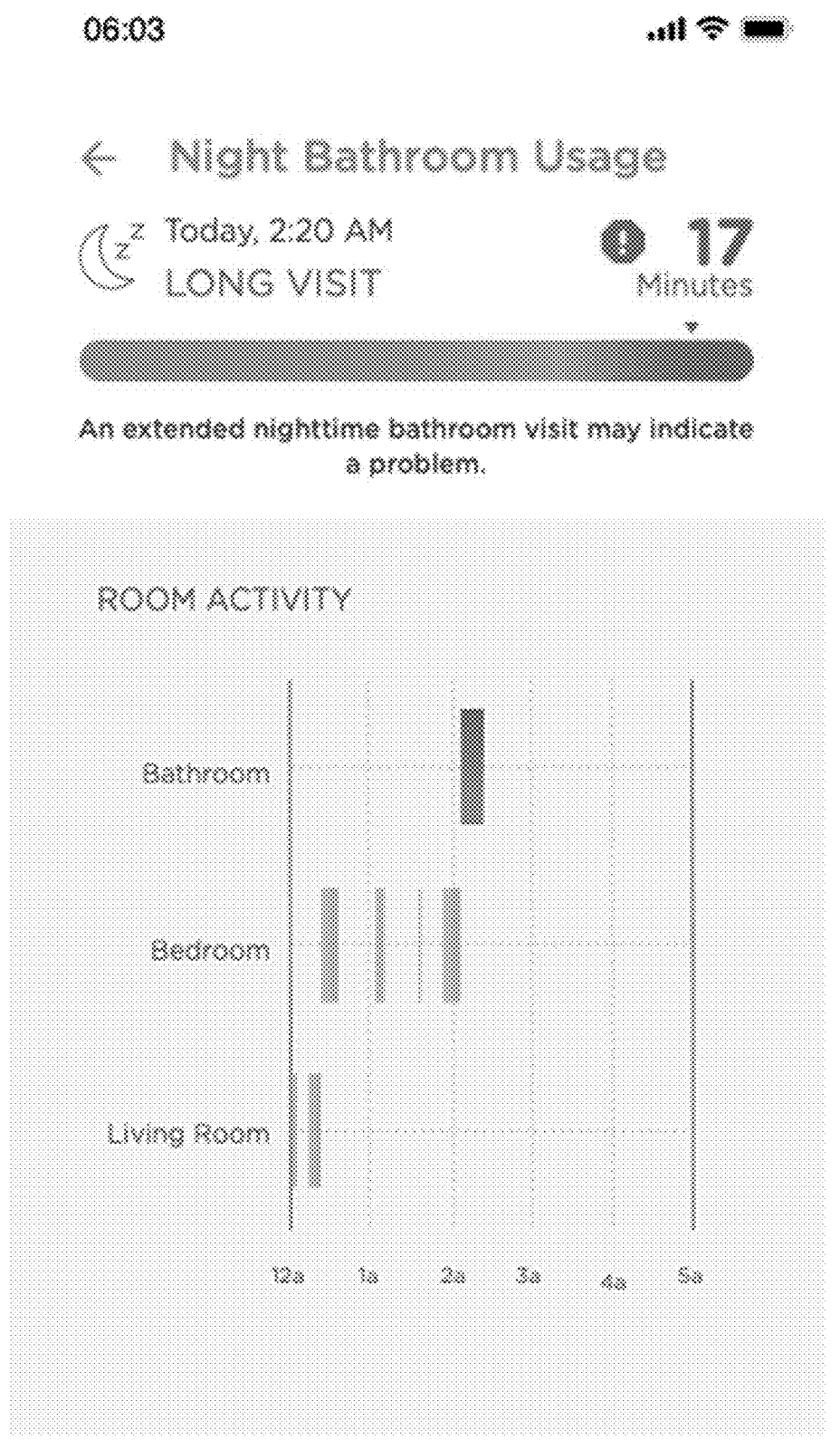

FIGS. 7A-7M details exemplary notifications generated by the system.

FIGS. 8A-8G show exemplary mobile client dashboards, while

DESCRIPTION

Figure 1A:
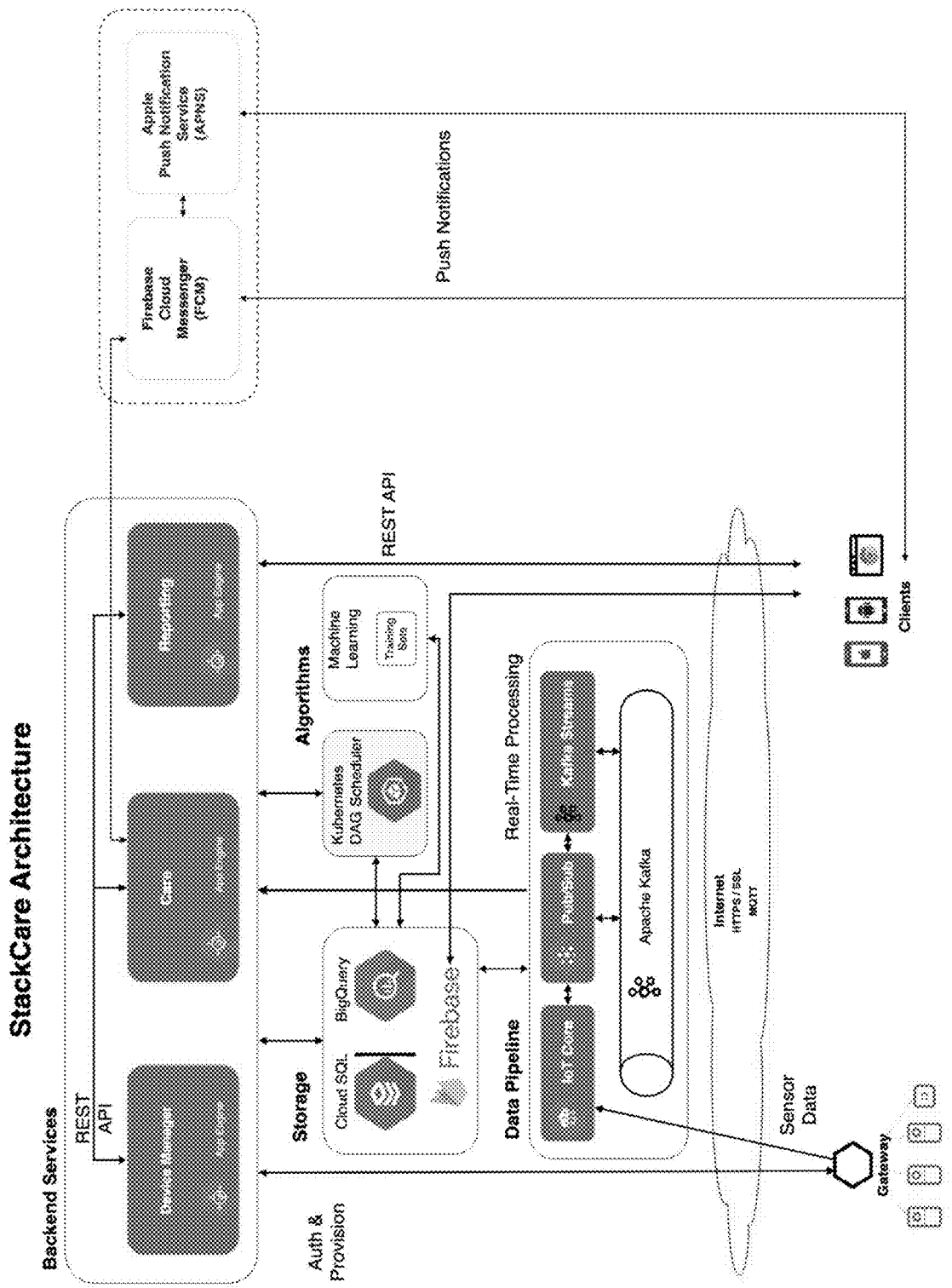
FIG. 1A shows an exemplary topology of a wellness monitoring architecture to help families monitor a person such as an elder.
Figure 1B:
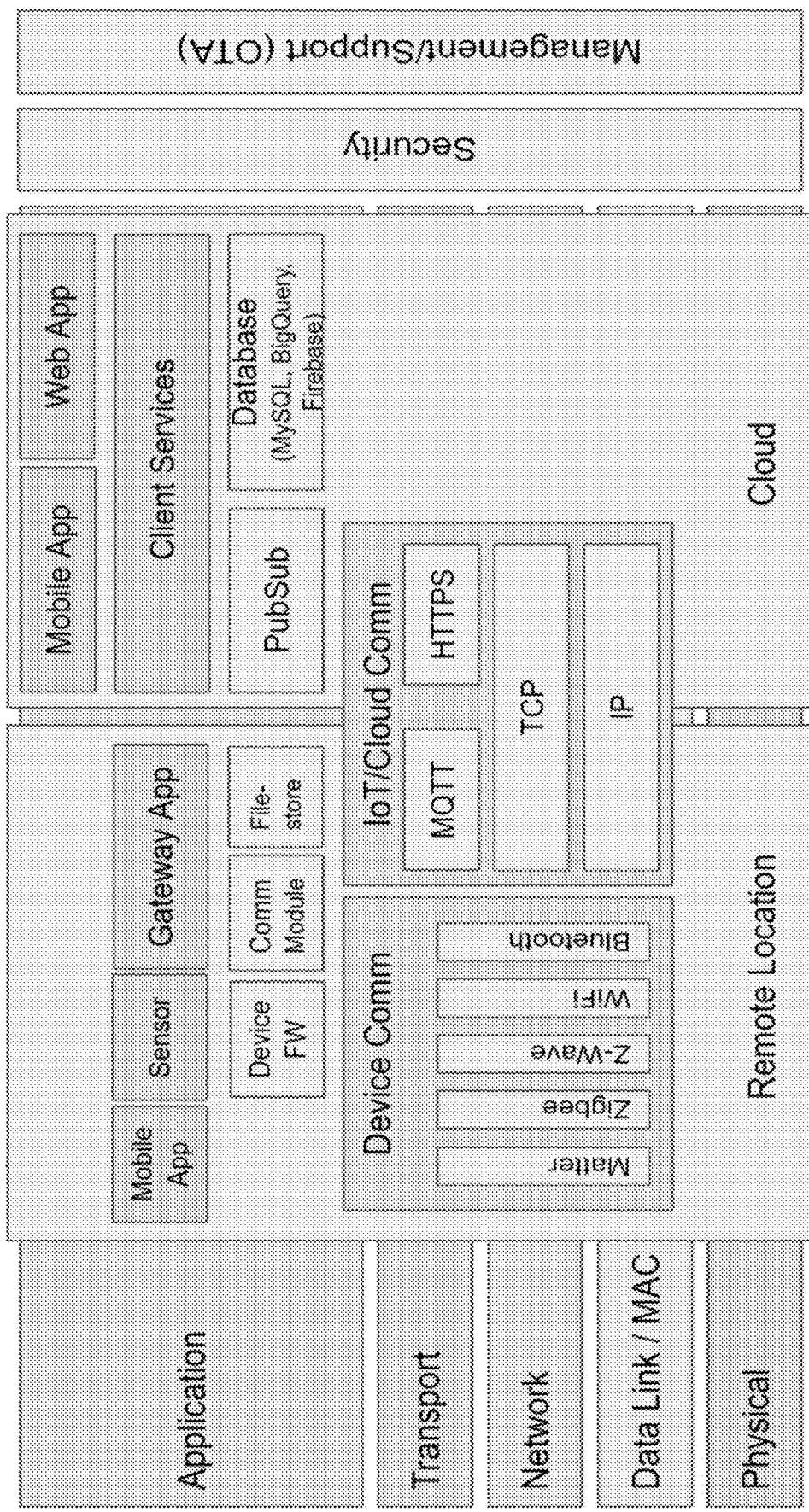
FIG. 1B shows exemplary with a robust and distributed architecture that uses various technologies to provide its monitoring services.

FIG. 1A-1B show an exemplary wellness monitoring architecture with a robust and distributed architecture that uses various technologies to provide its monitoring services. In this system, backend services communicate via REST API, cloud storage such as Firebase cloud storage, and AI machine learning. Wireless sensors such as Zigbee sensor devices are positioned at predetermined spots in a building or a home, and the sensors communicate sensor data through one or more gateways that provide data to a data pipeline with real-time processing as Kafka streams. Backend services communicate with mobile clients using the REST API and push notifications The architecture includes Zigbee sensor devices that communicate with a gateway to provide real-time data to a data pipeline that uses Kafka streams for processing. This allows for continuous monitoring and analysis of the data to detect any changes in an individual's health status or activity levels.

The data pipeline in turn communicates with a storage system that includes a cloud SQL database and BigQuery, for example. The use of Firebase Cloud Storage, DAG (Directed Acyclic Graph) scheduler, and AI machine learning enables remote monitoring capabilities and provides more personalized care.

The backend services communicate with mobile clients through a REST API, allowing caregivers or family members to remotely monitor an individual's health status and receive push notifications for any changes or alerts.

Clients such as caregivers and family members can send push notifications to a database messenger service (such as a Firebase Cloud Messenger) and a mobile push notification service (such as Apple PNS), which in turn communicates with a care app engine and a reporting engine, and the reporting engine can communicate with the client mobile devices.

The architecture provides a comprehensive and scalable solution for elderly monitoring, combining real-time data processing with advanced technologies to ensure the safety and well-being of elderly individuals while providing peace of mind for their caregivers and family members.

Figure 1C:
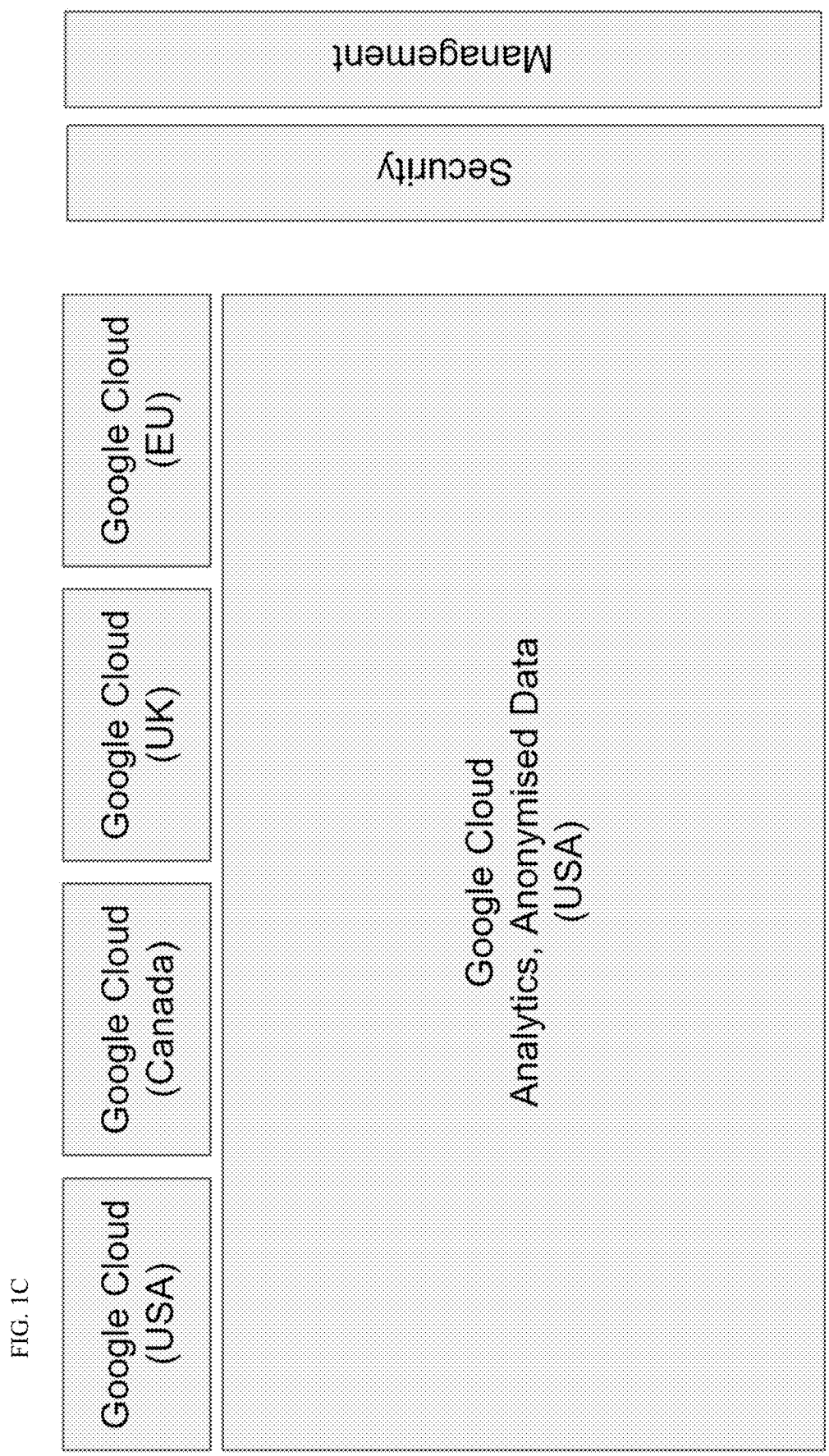
FIG. 1C shows a system to provide worldwide support.

FIG. 1C shows a system to provide worldwide support. The system includes Google Cloud for a plurality of regions including US, Canada, UK, and Europe. The system provides cloud analytics with anonymized data, security, and management.

Figure 1D:
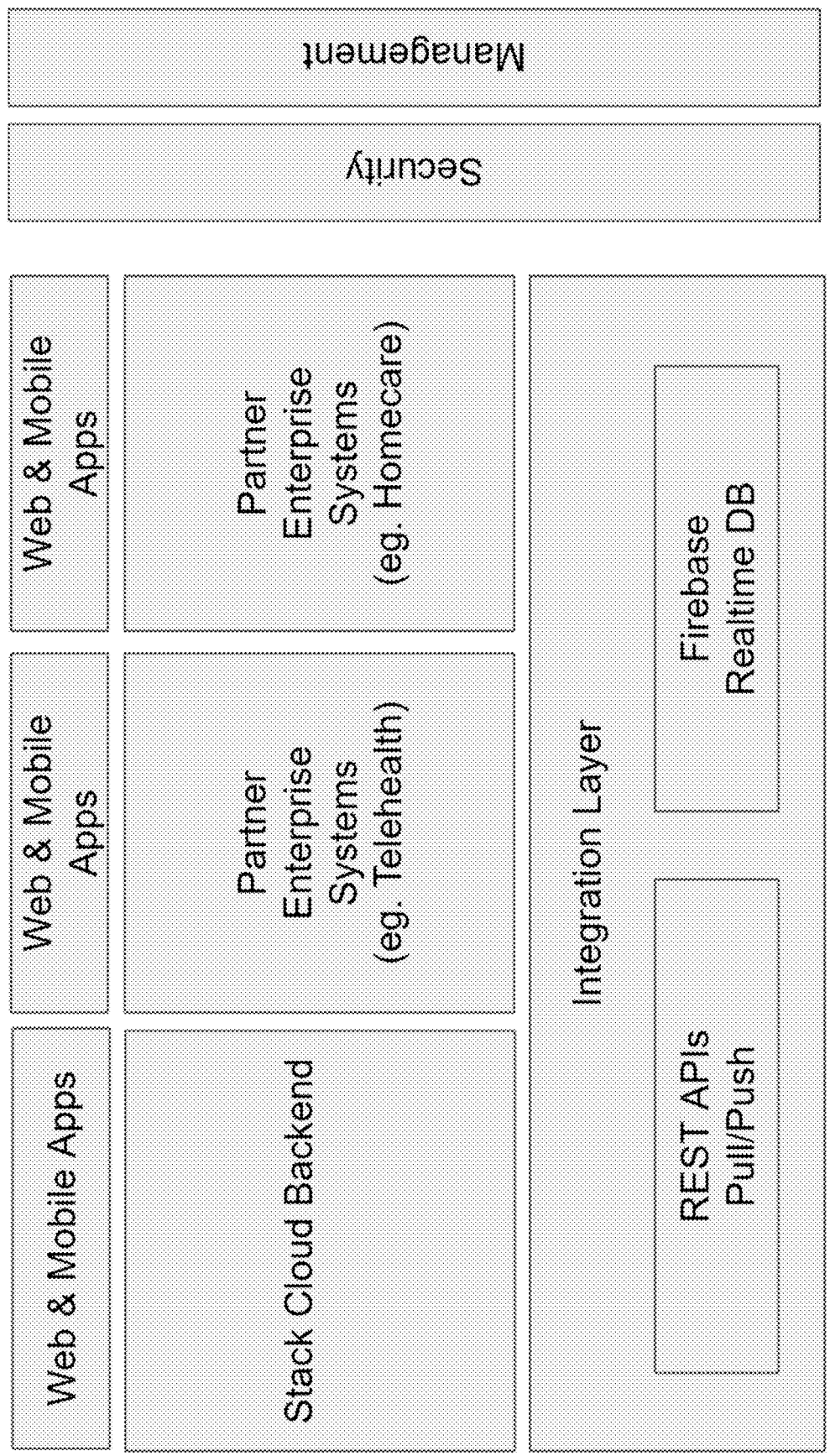
FIG. 1D shows an exemplary illustration of integration services supporting wellness monitoring.

FIG. 1D shows an exemplary illustration of integration services supporting wellness monitoring. The system includes an integration layer that receives REST API calls that pulls or push information to a realtime database (Firebase). The integration layer communicates with the cloud backend of FIGS. 1A-1B and additionally communicate with telehealth enterprise systems and partner home care systems. These systems can communicate over the web and also through mobile apps. Security and management is provided for the integration layer in accordance with procedure and compliance regulations such as HIPAA.

The system improves processor performance by offloading the real-time stream processing tasks to dedicated Kafka brokers and Kubernetes clusters, which are specifically designed to handle high throughput and low latency data processing. This allows the main processor to focus on other tasks, such as running backend services and machine learning algorithms, without being overwhelmed by the continuous flow of incoming data. Additionally, the use of SQL and BigQuery for batch analysis and processing allows for efficient handling of large amounts of data, further improving processor performance. Overall, by distributing the processing load across multiple specialized components and using efficient data processing techniques, the system is able to greatly improve processor performance and scalability.

FIG. 1E shows an exemplary app engine. The app engine handles care related tasks and the device manager, and is Stateless. It automatically scales horizontally based on request load, and can provide seamless Version Traffic Migration and Rollback. In one embodiment it is Python3 with Flask-Web Framework. The REST APIs supported include GET/POST/PUT/DELETE, Push Notifications, and Invitation & Event Escalation Emails.

The device manager is responsible for everything device-related and handles the Sites, Gateways, Zones, Devices (e.g. sensors, buttons), SIM Cards, and can handle OTA Management and Cloud IoT (MQTT Connection Management).

For OTA management, the device manager handles Versions/Images per gateway/device, Auto-detect down-revved gateways/devices, Push OTA down to gateways when needed, and Update device versions on successful OTA. It also handles Gateway Firmware OTA, Coordinator Firmware OTA, and Device Firmware OTA.

Figure 2:
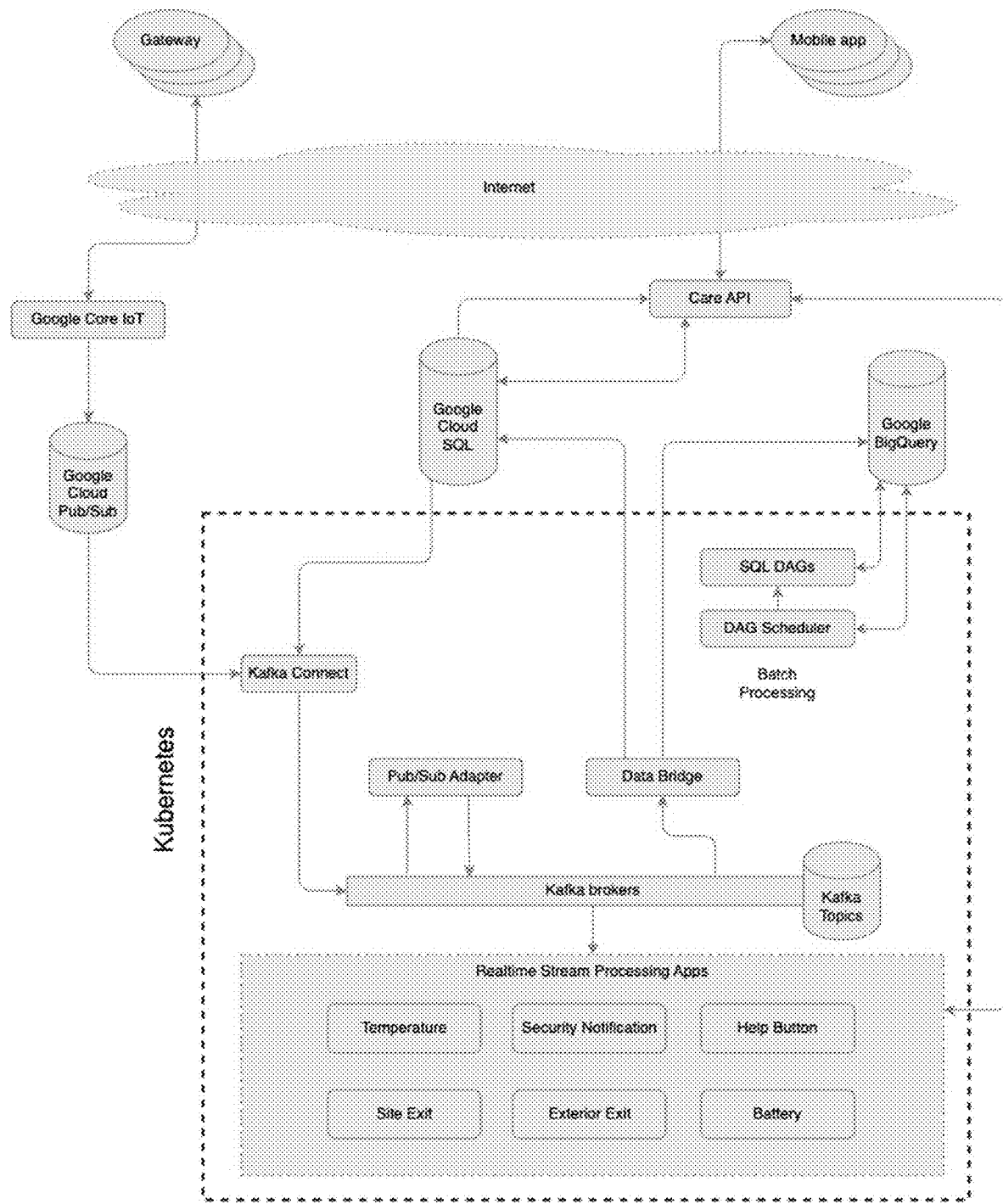
FIG. 2 shows an exemplary data pipeline that uses web data brokers to handle real-time stream processing apps.

In one implementation, the mobile clients has the following features:
   IOS/Swift
   Android/Kotlin
   Consumer & Pro UIs
   Localization
      English (US), English (UK), French, German, Spanish, Dutch
   API Calls
      HTTPS/OAuth2
   Firebase
      Real-time Updates FIG. 2 shows an exemplary data pipeline that uses Kubernetes and Kafka brokers to handle real-time stream processing apps for temperature, security notification, help request button, site exit, exterior exit, refrigerator door openings, and battery conditions, for example. The data pipeline architecture shown in FIG. 2 seems to be a sophisticated and robust solution that can handle real-time data processing and analysis, allowing for the continuous monitoring of an individual's health status and safety. The Kubernetes and Kafka brokers support a data pipeline that can handle real-time stream processing applications for various types of data, including temperature, security notifications, help requests, site exits, and exterior exits.

Kubernetes is a container orchestration platform that can help automate the deployment, scaling, and management of containerized applications. Kafka brokers are part of the Apache Kafka distributed streaming platform that can handle high-throughput, real-time data feeds.

The use of Kubernetes and Kafka brokers in the data pipeline creates a scalable and reliable infrastructure for wellness monitoring services. The real-time stream processing applications for various types of data, including temperature, security notifications, help requests, site exits, exterior exits, and battery condition monitoring provide a comprehensive monitoring solution that covers different aspects of an individual's well-being.

Apache Kafka is a distributed, highly scalable, elastic, fault-tolerant, and secure system that stores data in change feeds. It also provides event-time and exactly-once processing with joins, aggregations, filters, transformations, and more.

The IoT core Publication subscription enables the system to publish data from devices to a Cloud Pub/Sub topic. Messages sent to this topic are delivered to any clients that subscribe to it. This publish-receive flow implements the publisher-subscriber pattern, which allows loosely coupled and scalable architectures. IoT Core uses the MQTT protocol for messaging subscriptions and publishing transport. This lightweight M2M connectivity protocol supports X.509 certificates with TLS authentication for secure messages transfer. Alternatively, the system can use ClearBlade IoT Core which is a fully managed service for securely connecting and managing IoT devices. The IoT Core supports multiple topics and can be configured to use wildcards and pattern matching. Devices can subscribe to a topic and read all messages that are published to it, or they can unsubscribe from a specific topic. IoT Core policies to specify how a device can publish or subscribe to topics, and conditions and variables can be specified. IoT Core provides a Device Gateway that manages all active device connections and a Message Broker that securely transmits messages to and from devices with low latency. The Message Broker is based on the MQTT protocol, and supports a variety of Quality of Service (QOS) levels. IoT Core also includes a telemetry stream that is used to monitor device health or metrics. It is pushed to Amazon OpenSearch, which can be used for dashboarding or other applications. IoT Core supports both the MQTT QoS level 0 and the MQTT QoS level 1. In general, it is recommended to use the QoS level 1 for IoT devices that connect over intermittent or slow network connections, because it guarantees at least once delivery of a message. As with any IoT application, balancing the frequency of messages sent to the cloud against your devices 'limitations is crucial. Ideally, you want to send a message back to the cloud whenever your devices connect and are sending meaningful data.

One implementation encrypts the payload, which reduces the cost of sending a message. However, this may have a significant impact on the message's transmission time. You can mitigate this by leveraging local processing to aggregate data points and sending them to the cloud instead of sending all of the original data.

The first step in implementing an IoT Analytics pipeline is to read data from sensors with the IoT Core endpoint. Devices connect to the endpoint via MQTT, then publish messages to a topic for that device or sensor. IoT Core translates the data into a format that is usable by the cloud service. Once the data is in the cloud the system performs processing on it. Generally, the system filters out certain values from the data and then transforms it before sending it to a data warehouse. This data will need to be stored for a certain period of time using cloud storage. The IoT Analytics Pipeline will ingest these data from the S3 bucket and then execute some transformations on it. After the data has been transformed, it will be sent to the IoT Analytics Datastore. This is a materialized view that can be used by other services to display visualizations and dashboards.

Streaming data is a type of IoT data that is generated continuously by thousands or even billions of connected devices and is a constant source of new knowledge. Streaming analytics can help businesses find meaningful patterns and uncover new knowledge in real or near-real-time.

The IoT Core Machine Learning service is a component of the Google Cloud Platform (GCP) that uses a variety of cloud-based tools to help you collect, analyze, and manage IoT data. IoT Core ML can help the system detect and predict anomalies in the data that the sensor sends. Using ML to analyze data from sensors can also provide insights that cannot be detected by traditional means. This helps the system identify and prevent issues that may cause person to be in a dangerous condition where help is needed.

The IoT Core ML service works by consuming data from sensors that are provided to the GCP Cloud infrastructure through a series of Kafka streams. This allows the system to create a data pipeline that transforms the messages through a series of activities before they are stored in the demonstration's data store.

Figure 3:
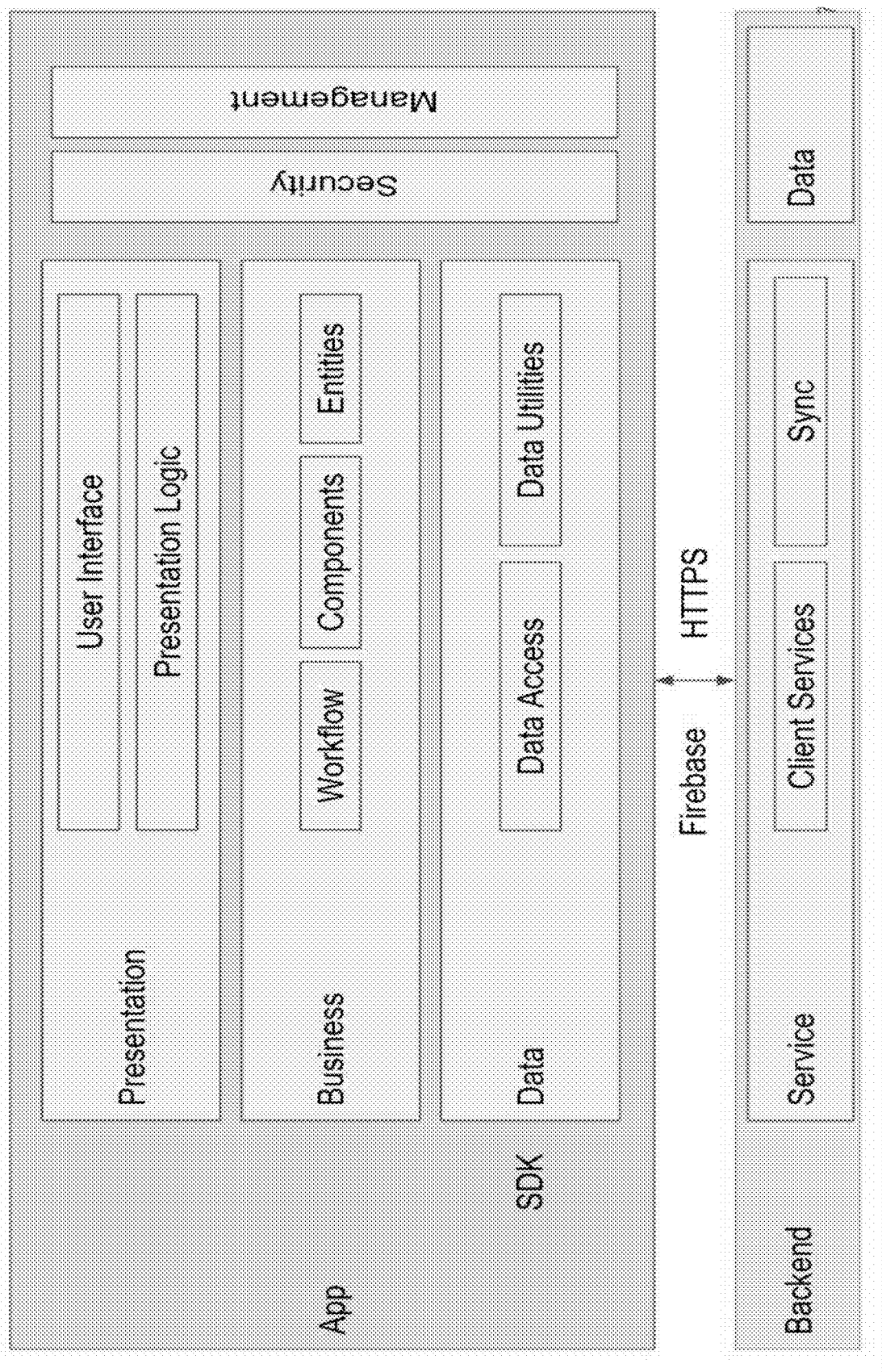
FIG. 3 shows an exemplary Web/Mobile Client Architecture with Backend Services communicating with App with Data, Presentation, and Business layers, among others.

FIG. 3 shows an exemplary Web/Mobile Client Architecture with Backend Services communicating with App with Data, Presentation, and Business layers, among others.

The data layer is responsible for managing data storage and retrieval, while the presentation layer handles the user interface (UI) and user experience (UX) components of the app. The business layer sits in between the data and presentation layers, providing logic and functionality to the app.

The backend services communicate with the app through these layers, allowing for a separation of concerns and facilitating efficient communication between the client and server. This architecture can help to ensure that the app remains responsive and reliable, even when dealing with large amounts of data or complex processing tasks.

The client-server architecture shown in FIG. 3 provides a user-friendly and reliable experience for StackCare's web and mobile clients. The separation of concerns between the data, presentation, and business layers can help to ensure that the app is scalable, efficient, and easy to maintain, while also providing a high level of functionality and interactivity for the end-user.

Next, the Kafka Stream Apps-Real-Time Algorithms are detailed. Kafka stream apps are applications that are built on top of Apache Kafka's stream processing framework, which allows for real-time processing of data streams. These apps can utilize real-time algorithms to analyze and process the data as it flows through the Kafka stream.

Real-time algorithms are algorithms that can provide immediate results, without requiring the entire dataset to be processed first. They are often used in stream processing applications, where data is continually flowing and needs to be analyzed in real-time. Real-time algorithms can help to detect patterns, anomalies, or other events of interest as they occur in the data stream, allowing for prompt action to be taken.

Some examples of real-time algorithms that can be used in Kafka stream apps include anomaly detection algorithms, clustering algorithms, decision tree algorithms, and regression algorithms. These algorithms can be used to perform various tasks, such as identifying abnormal sensor readings, grouping similar data points together, predicting future values, or classifying data into different categories.

The use of real-time algorithms in Kafka stream apps can help to provide valuable insights and enable quick decision-making based on the data. This can be particularly useful in elderly monitoring systems, where timely detection of health issues or safety concerns can be critical. The Kafka stream apps with real-time algorithms can provide a powerful solution for processing and analyzing data in real-time, enabling more effective monitoring and management of elderly care. In one implementation, the system provides
  A stream app for each real-time algorithm
  Directly consume motion/contact/attribute data
  Trigger notifications "immediately" depending on criteria
  Used when batch analysis is not fast enough
  Notifications with Help Button Press, Temperature Warning, Site Exit, Exterior Door, Security The system provides a Kafka stream app architecture that allows for real-time processing of motion, contact, and attribute data to trigger notifications based on certain criteria. This is a great approach for providing immediate alerts and taking action when the batch analysis is not fast enough. The system uses defined specific criteria for triggering notifications, such as Help Button Press, Temperature Warning, Site Exit, Exterior Door, and Security. These are all important events that can indicate potential issues or risks to the well-being of elderly individuals, and it's essential to have a system in place to detect and respond to them promptly.

By utilizing a stream app for each real-time algorithm, the system can ensure that each notification is triggered based on accurate and up-to-date information. This can help to reduce false alarms and ensure that caregivers or family members can take action quickly when necessary. In this manner, the system provides timely alerts and ensures the safety and well-being of elderly individuals.

Figure 4:
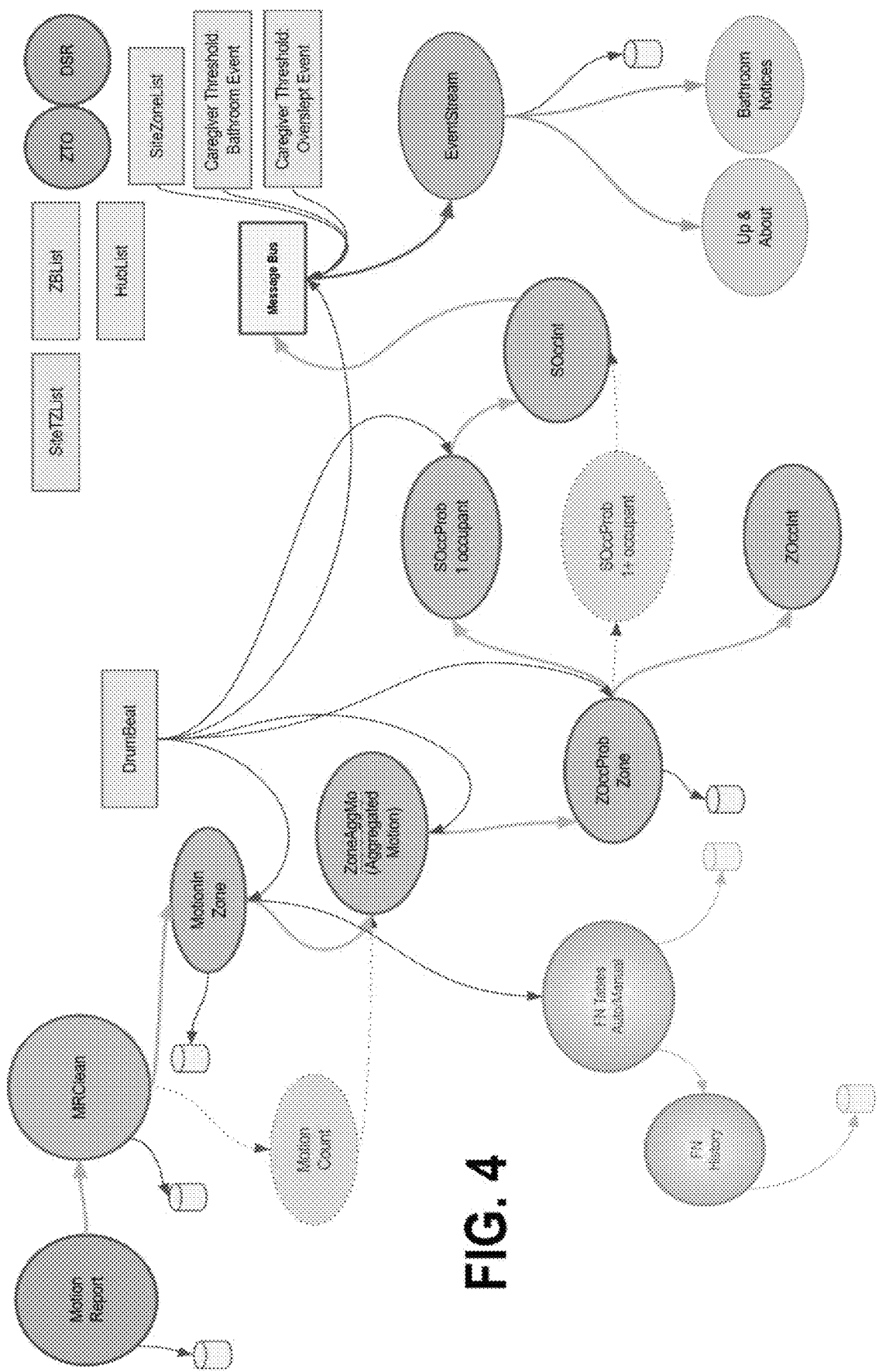
FIG. 4 shows an exemplary Directed Acyclic Graph (DAG) for wellness checking.

Next, details on the DAGs are provided. In one implementation, the system provides the following:

A DAG for 5-minute or hourly (Motion Processing/Bathroom Visits)
When several minute delays are not life-threatening
Efficiently handled for a large number of sites
Implemented in SQL and executed by BigQuery for scalability FIG. 4 shows an exemplary Directed Acyclic Graph (DAG) for wellness checking. In this implementation, the DAG is designed for 5-minute or hourly motion processing and bathroom visit tracking. This approach is suitable when several minute delays are not life-threatening, and it is can handle a large number of sites efficiently.

By using a DAG, the system can break down the processing and tracking of motion and bathroom visits into smaller, manageable tasks that can be executed in parallel. This can help to improve processing efficiency and reduce the risk of delays or bottlenecks.

The system has also chosen to implement this processing and tracking using SQL and execute it using BigQuery, which is a scalable and efficient solution for handling large amounts of data. By leveraging the power of BigQuery, the system can ensure that the processing and tracking of motion and bathroom visits can be scaled to handle a large number of sites efficiently.

Overall, the DAG for motion processing and bathroom visit tracking, along with the implementation of SQL and BigQuery, enables managing and analyzing large amounts of data efficiently and effectively.

Motion processing involves analyzing motion data to extract useful information and insights. The system handles four tasks that can be performed as part of motion processing: cleanup, motion activity, zone occupancy, and bathroom visits.

Cleanup: This involves removing any noise or irrelevant data from the motion data stream to ensure that only meaningful data is analyzed. This can help to improve the accuracy of subsequent processing steps.

Motion Activity: This task involves analyzing the motion data stream to identify periods of activity and inactivity. This information can be used to determine if an elderly individual is active and moving around, or if they are potentially immobile or unresponsive.

Zone Occupancy: This task involves analyzing motion data to determine which areas or zones of a site are occupied or unoccupied. This information can be used to track the movements of an elderly individual and identify if they are moving around the site or staying in a specific area.

Bathroom Visits: This task involves analyzing motion data to detect when an individual enters and exits a bathroom. This information can be used to track the frequency of bathroom visits and ensure that elderly individuals are maintaining their hygiene and health.

By performing these four tasks as part of motion processing, the system can gain valuable insights into the activity and movements of elderly individuals in their care. This can help to detect potential health or safety issues and provide timely assistance or intervention when necessary.

Next, notifications are detailed for wellness monitoring including Up & About Check, Bathroom Overstay, Night Bathroom Overstay, Night Bathroom Total Visits, Night Bathroom Total Time, Day Activity Monitor, Night Activity Monito, Kitchen AM, Bathroom Visit Count.

The system has identified several key notifications that can be triggered based on the results of motion processing and bathroom visit tracking. These notifications can help to detect potential issues or risks to the well-being of elderly individuals and prompt timely action by caregivers or family members. The notifications include:

Up & About Check: This notification is triggered when an elderly individual has been inactive or immobile for an extended period, indicating a potential issue or concern.

Bathroom Overstay: This notification is triggered when an elderly individual spends an unusually long time in the bathroom, which can indicate potential health or hygiene issues.

Night Bathroom Overstay: This notification is similar to the Bathroom Overstay notification, but specifically triggered during nighttime hours.

Night Bathroom Total Visits: This notification is triggered to track the frequency of bathroom visits during nighttime hours.

Night Bathroom Total Time: This notification is triggered to track the total time an elderly individual spends in the bathroom during nighttime hours.

Day Activity Monitor: This notification is triggered to track the activity level of an elderly individual during daytime hours, providing an overall picture of their movements and activity.

Night Activity Monitor: This notification is triggered when an elderly individual is active during nighttime hours, potentially indicating sleep disturbances or other issues.

Kitchen Activity Monitor: This notification is triggered when an elderly individual visits the kitchen during nighttime hours, which can indicate potential issues with nutrition or sleep.

Bathroom Visit Count: This notification tracks the frequency of bathroom visits during daytime hours.

Overall, these notifications provide valuable insights into the well-being and activity of elderly individuals in Stack-Care's care, helping to detect potential issues or concerns and prompt timely action.

Figure 5:
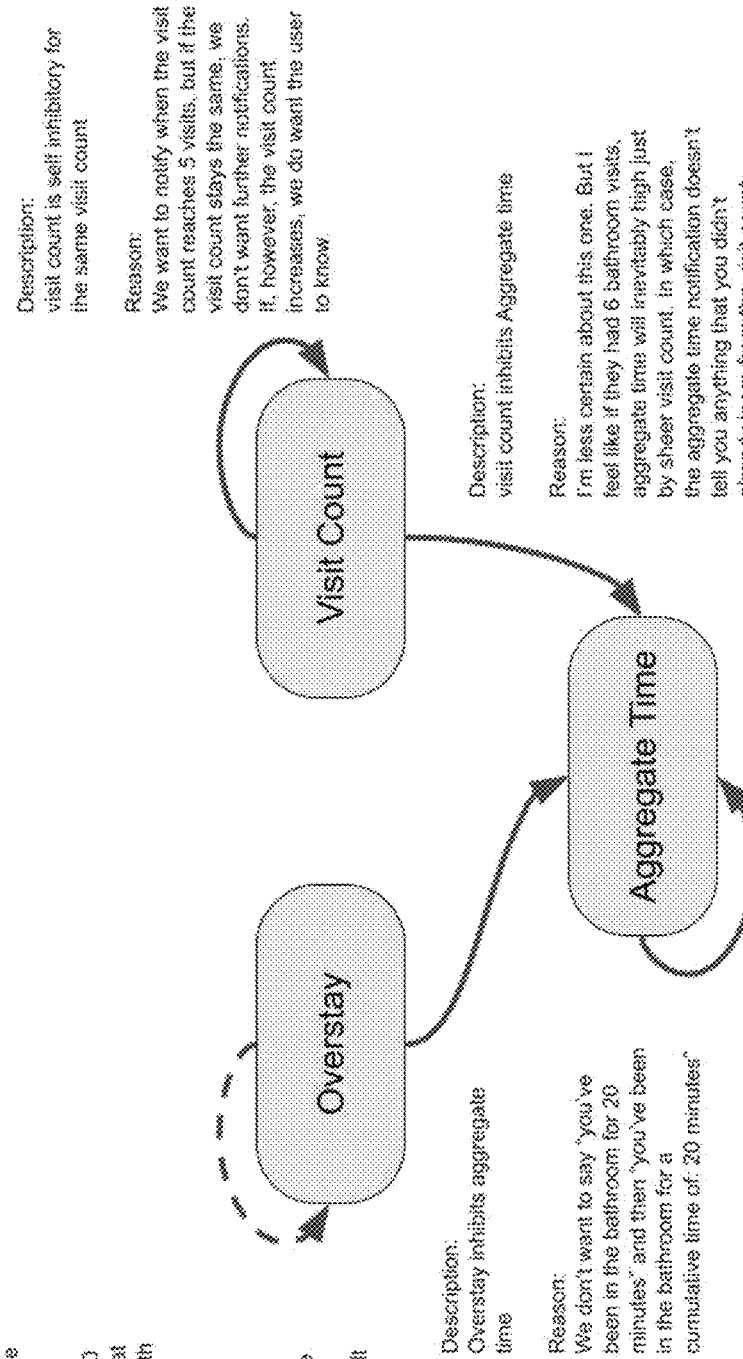
FIG. 5 shows an exemplary DAG for inhibiting wellness checking.

FIG. 5 shows an exemplary DAG for inhibiting wellness checking. The Inhibitions can be based on time or events. In one example, the conditions are as follows:
Time (how long since last event?)
Exterior Door—60 minutes
Help button—20 seconds
Night Activity Monitor—120 minutes Inhibitions are a way to prevent excessive or unnecessary notifications from being triggered based on motion processing and bathroom visit tracking. The system has identified several inhibitions based on time intervals, which help to ensure that notifications are only triggered when certain conditions persist for a certain period. These inhibitions include:

Exterior Door: This inhibition is set to 60 minutes, which means that notifications related to the exterior door will only be triggered if the door has been open for more than 60 minutes.

Help Button: This inhibition is set to 20 seconds, which means that notifications related to the help button will only be triggered if the button is pressed for more than 20 seconds. This helps to prevent false alarms or accidental triggers of the help button.

Night Activity Monitor: This inhibition is set to 120 minutes, which means that notifications related to nighttime activity will only be triggered if the individual has been active for more than 120 minutes during the night. This helps to prevent unnecessary notifications for short periods of activity or movement during nighttime hours.

These inhibitions help to ensure that notifications are triggered only when necessary and based on meaningful patterns of activity or behavior. This helps to reduce the number of false alarms or unnecessary notifications, while still providing valuable insights and assistance to caregivers and family members.

The inhibitions can be event based. Examples of Related Events can include:
  Night Bathroom Overstay—inhibits itself until visit is over
  Night Bathroom Total Time—Do not create if existing NBO or Night Bathroom Total Visits Related events are a way to ensure that notifications are triggered only when certain conditions are met, and to prevent unnecessary or redundant notifications. The system has identified two related events based on bathroom visit tracking, which help to ensure that notifications related to bathroom visits are triggered only when appropriate. These related events include:
  Night Bathroom Overstay: This event inhibits itself until the bathroom visit is over, which means that notifications related to bathroom overstays will not be triggered while the individual is still in the bathroom. This helps to prevent redundant notifications or unnecessary alerts.
  Night Bathroom Total Time: This event is not created if there is an existing Night Bathroom Overstay or Night Bathroom Total Visits notification, which means that notifications related to total time spent in the bathroom during nighttime hours will not be triggered if there is already a notification related to a bathroom overstay or frequent visits. This helps to prevent redundant or unnecessary notifications and ensures that notifications are triggered only when meaningful patterns of behavior or activity are detected.

Overall, these related events help to ensure that notifications related to bathroom visits are triggered only when necessary and based on meaningful patterns of behavior or activity. This helps to reduce the number of false alarms or unnecessary notifications, while still providing valuable insights and assistance to caregivers and family members.

Figure 6:
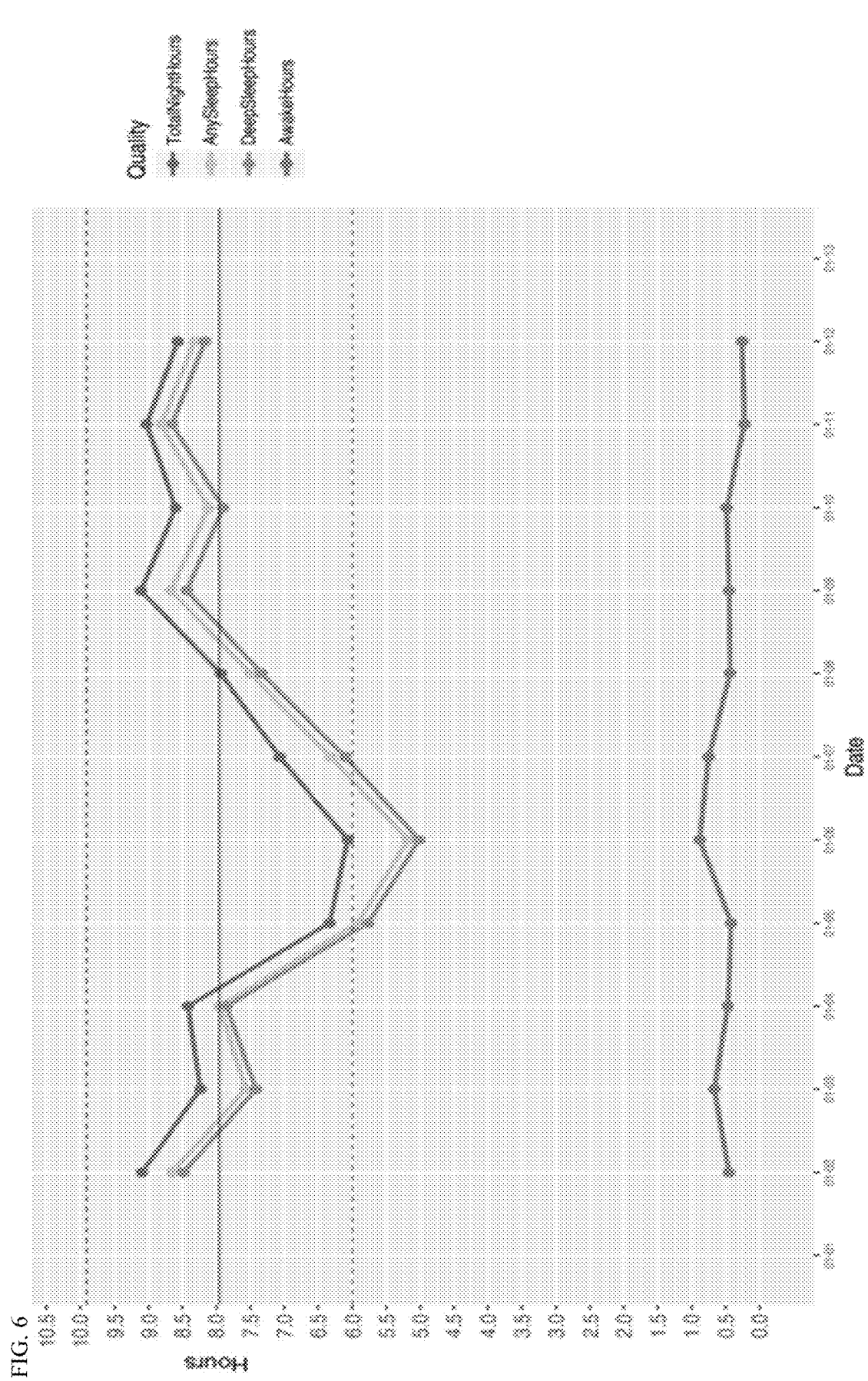
FIG. 6 shows an exemplary process to determine unusual bathroom visitations as a check on wellness.
Figure 7A:
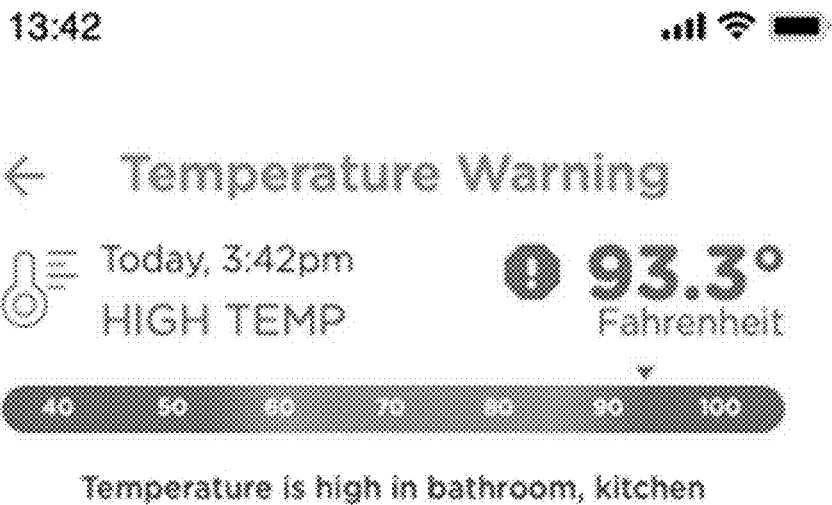
Figure 7A:
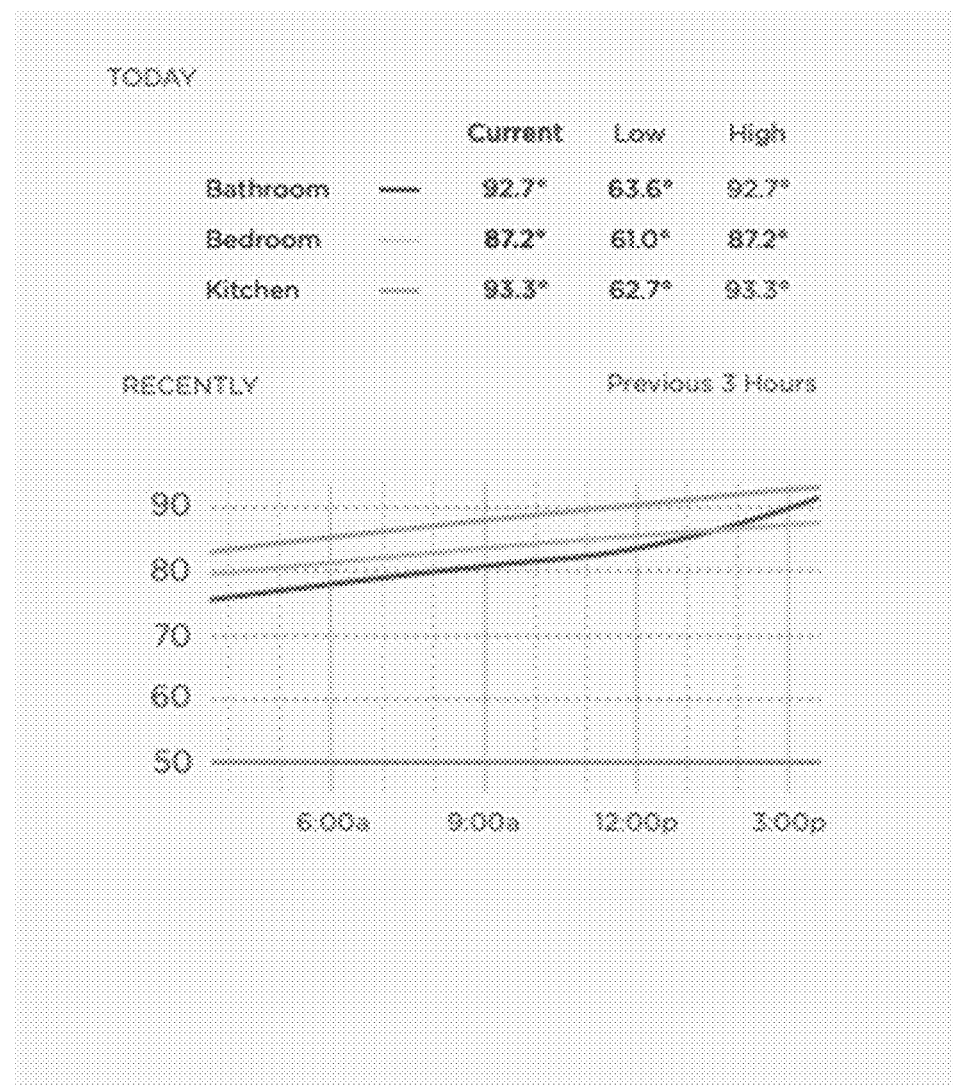
Figure 7B:
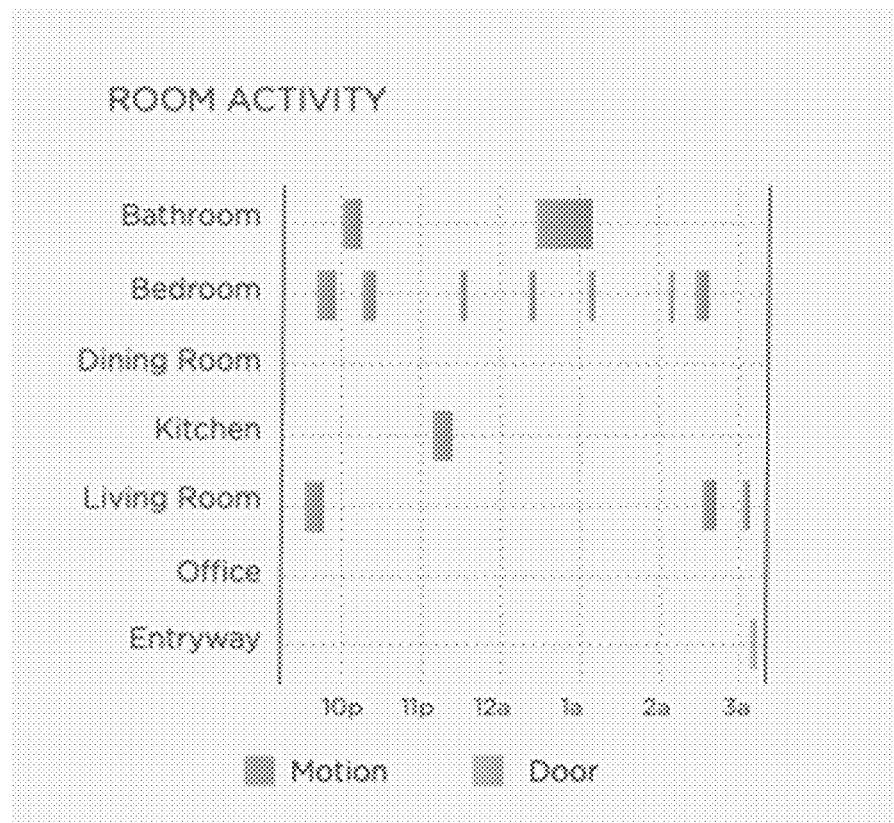
Figure 7D:
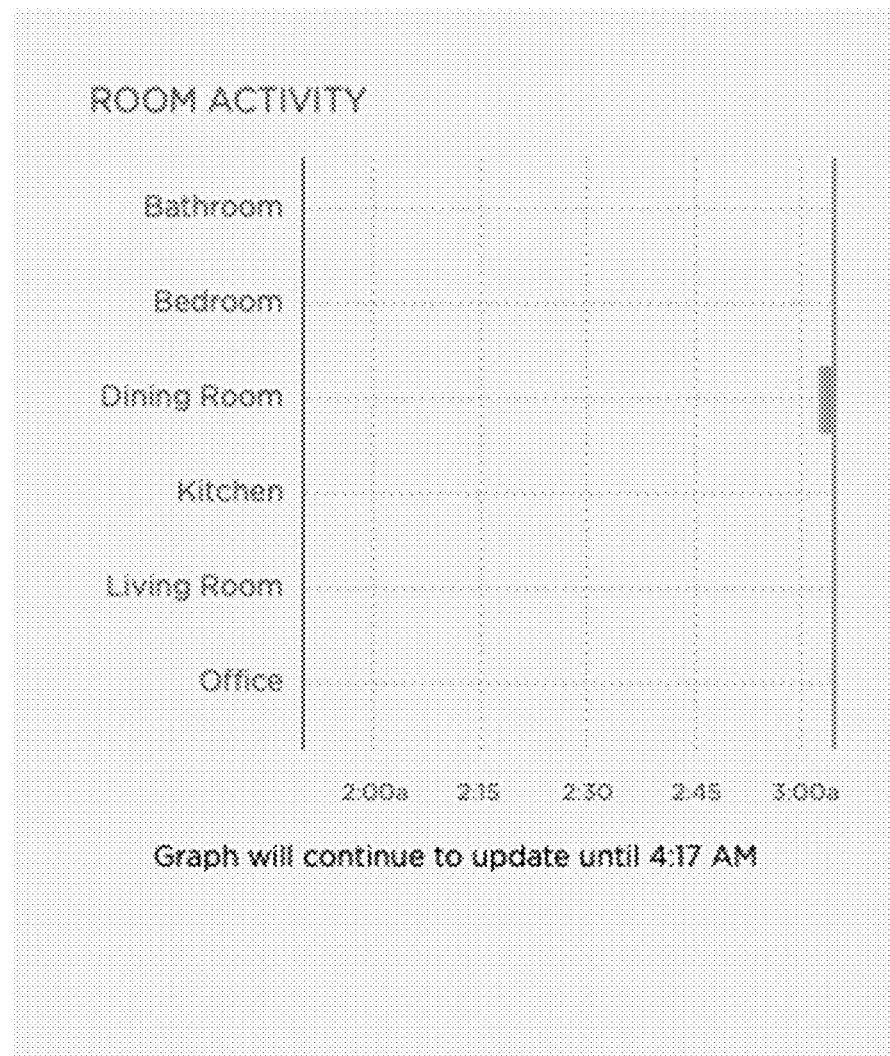
Figure 7E:
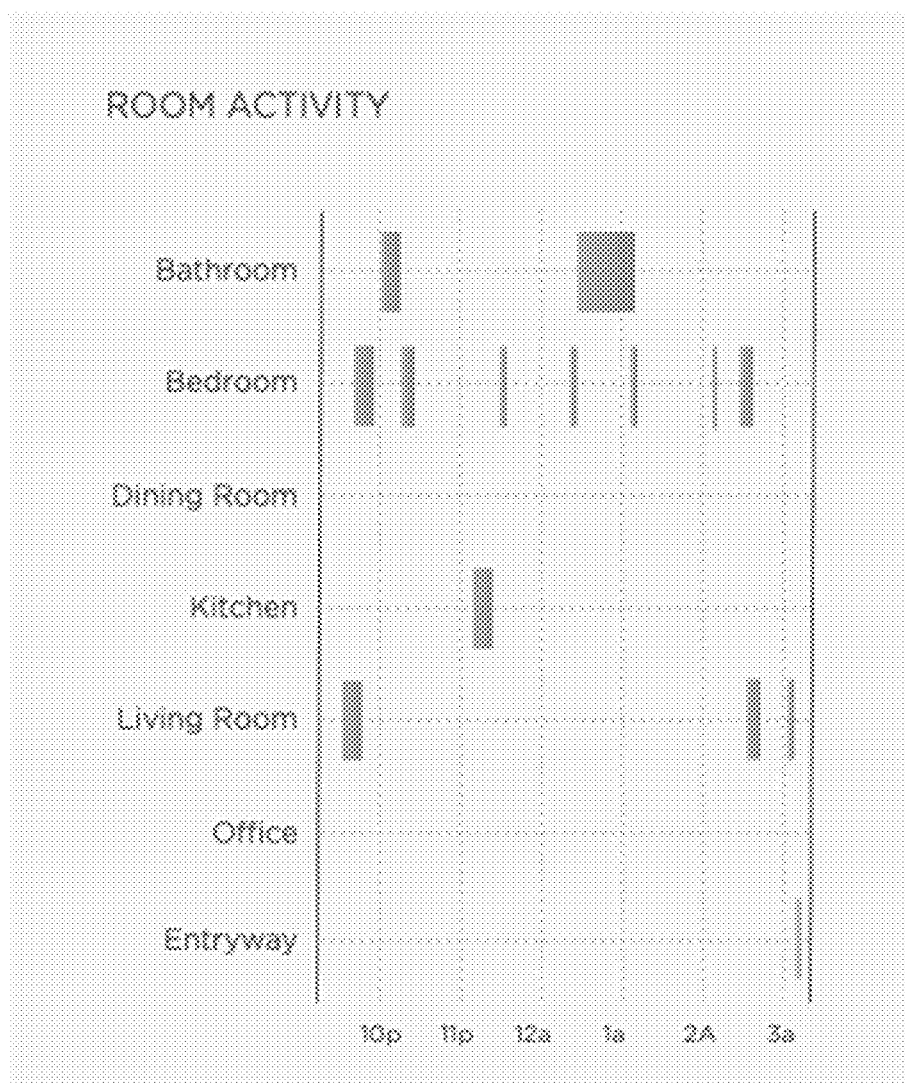
Figure 7F:
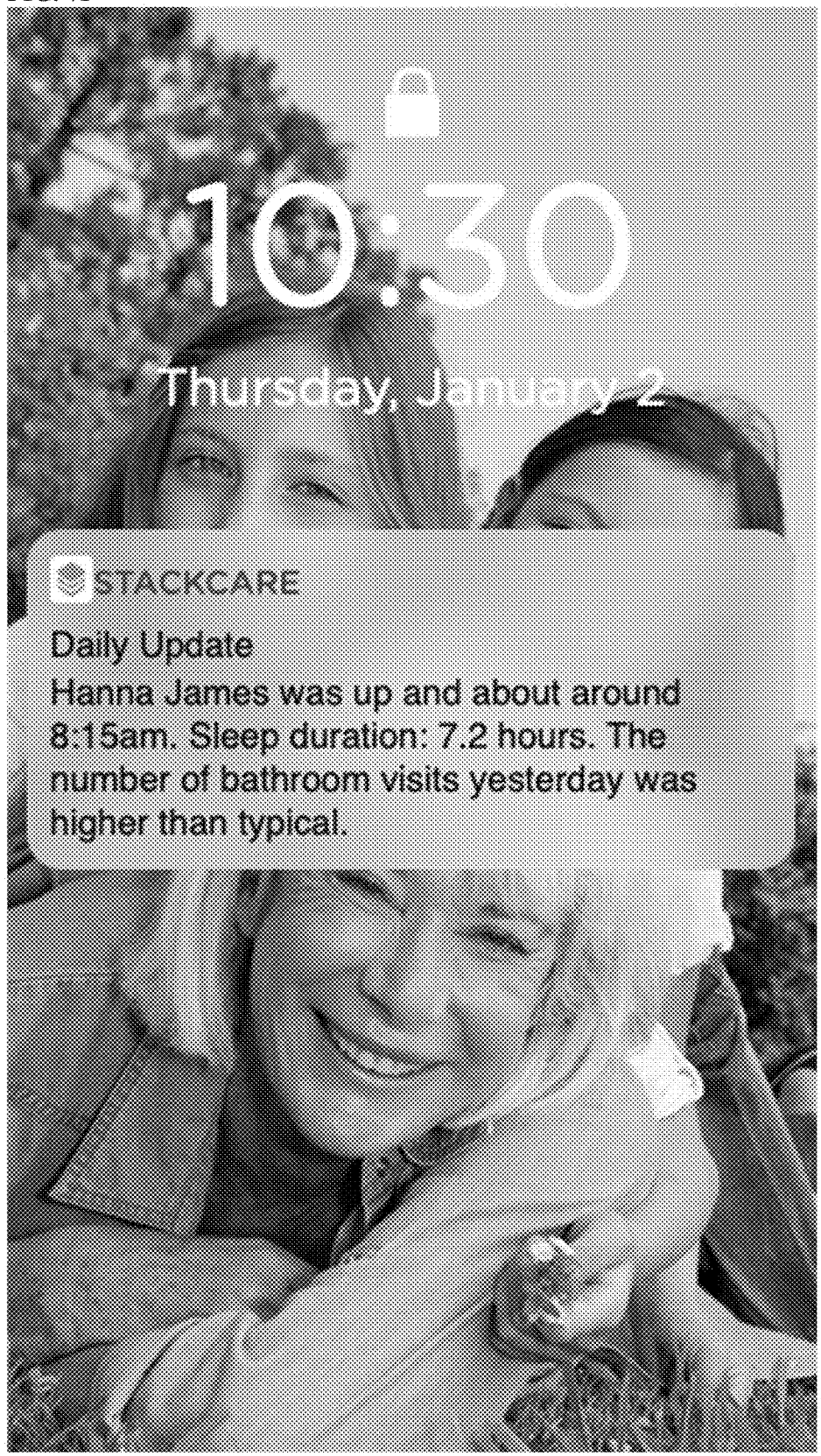
Figure 7G:
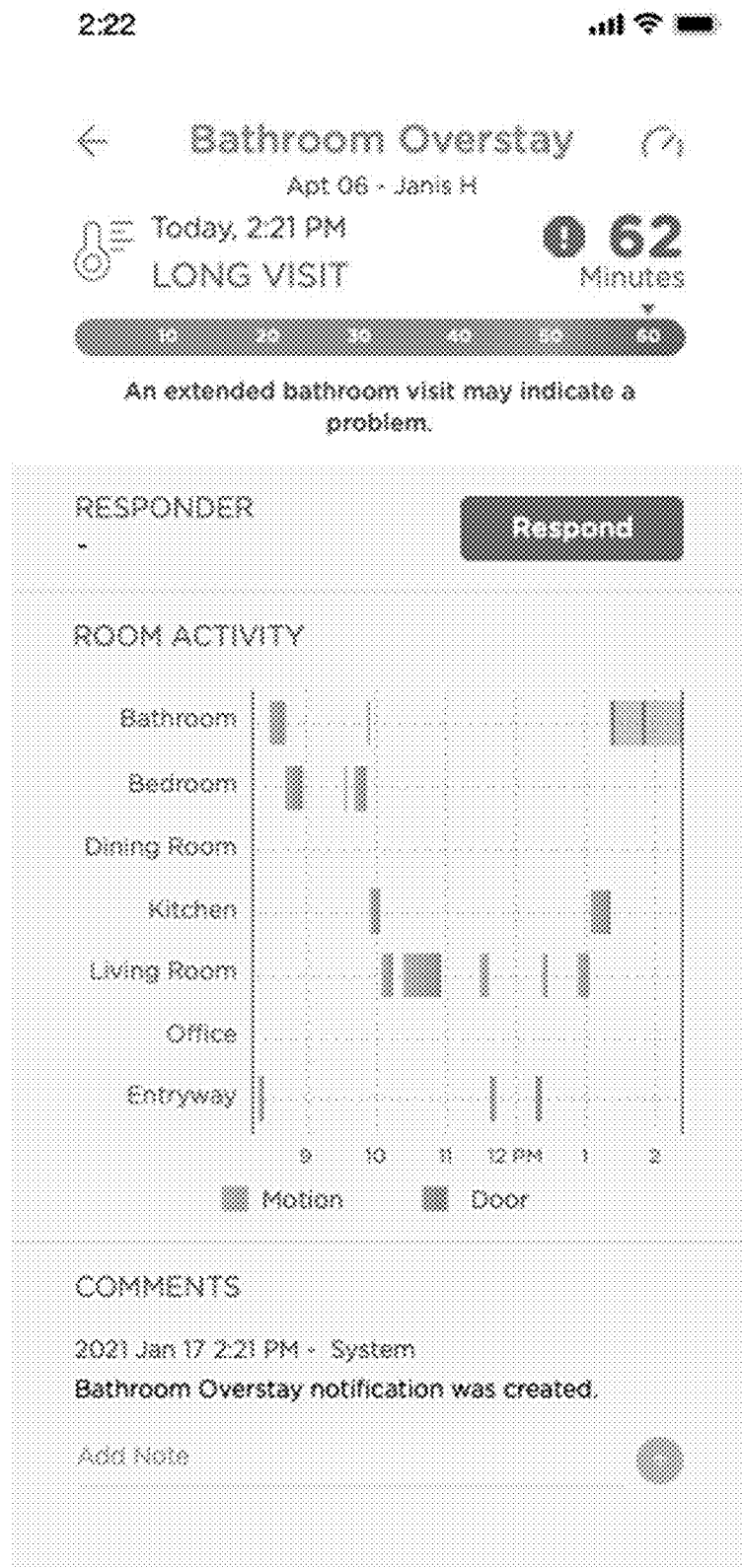
Figure 7H:
Figure 7I:
Figure 7I:
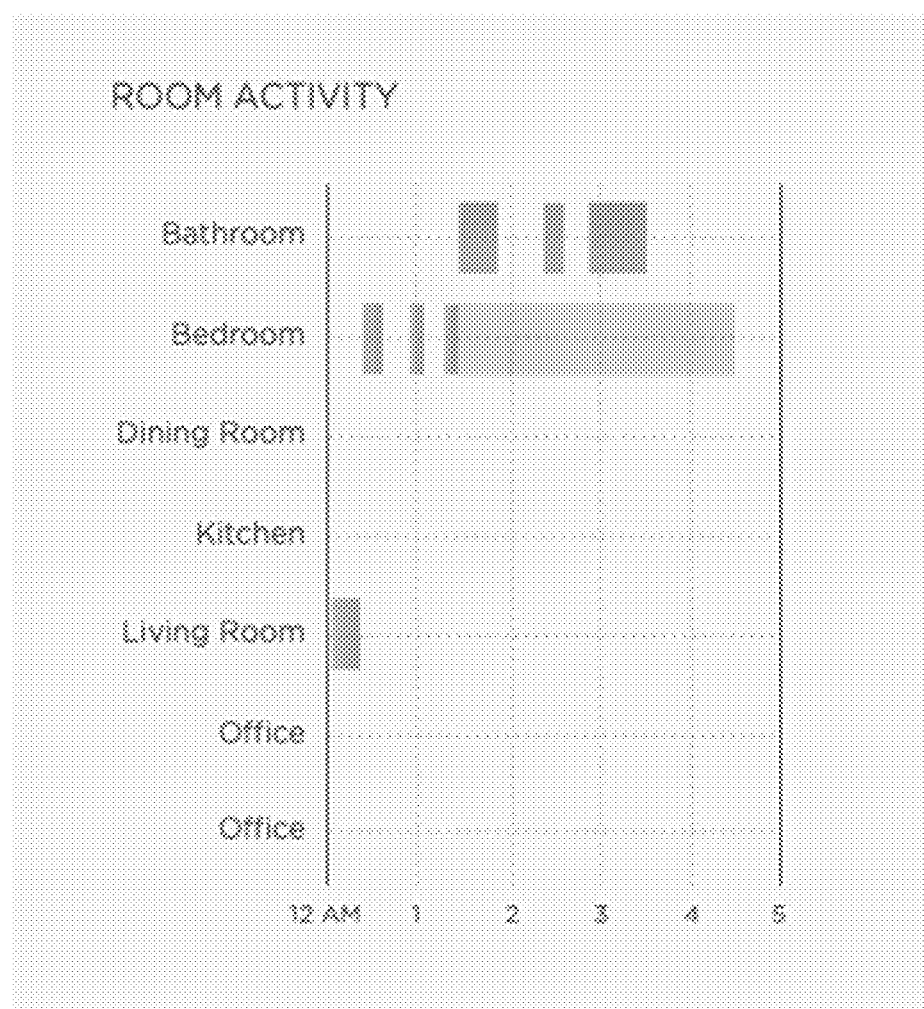
Figure 7J:
Figure 7L:
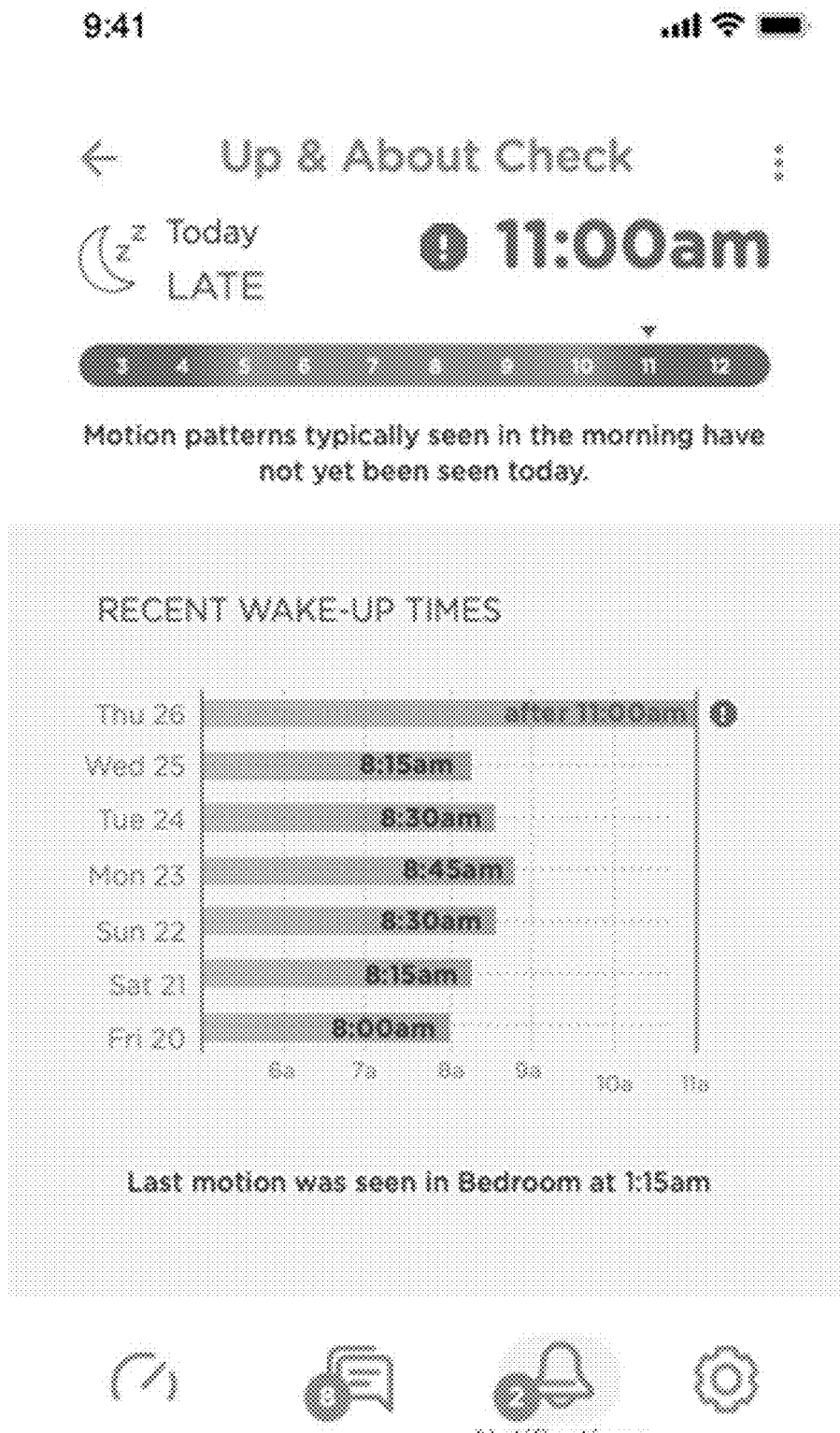
Figure 7M:
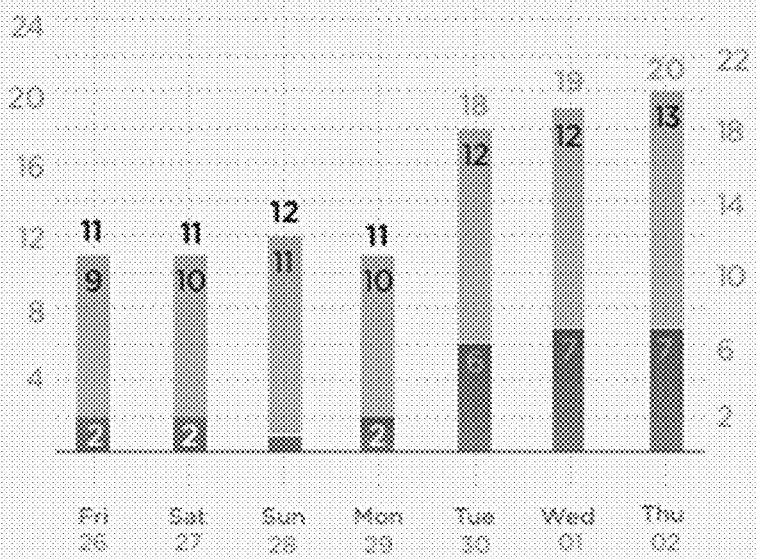
Figure 8A:
Figure 8B:
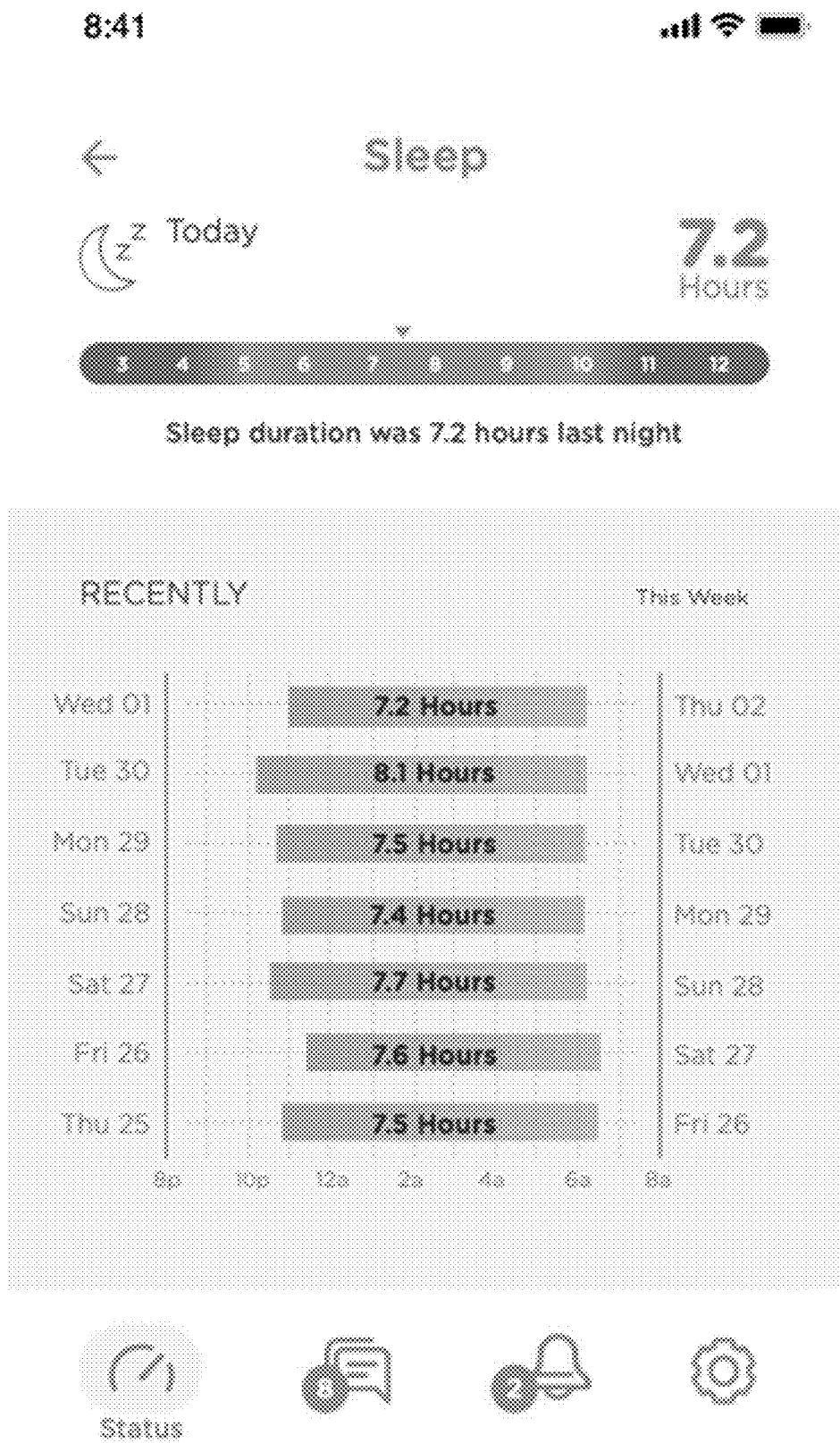
Figure 8C:
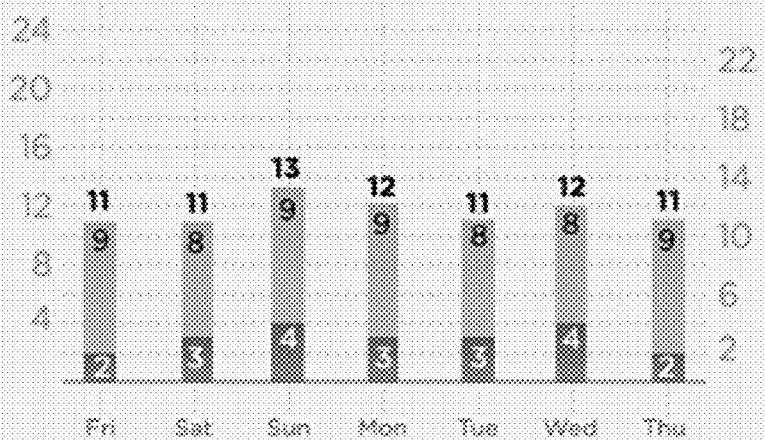
Figure 8D:
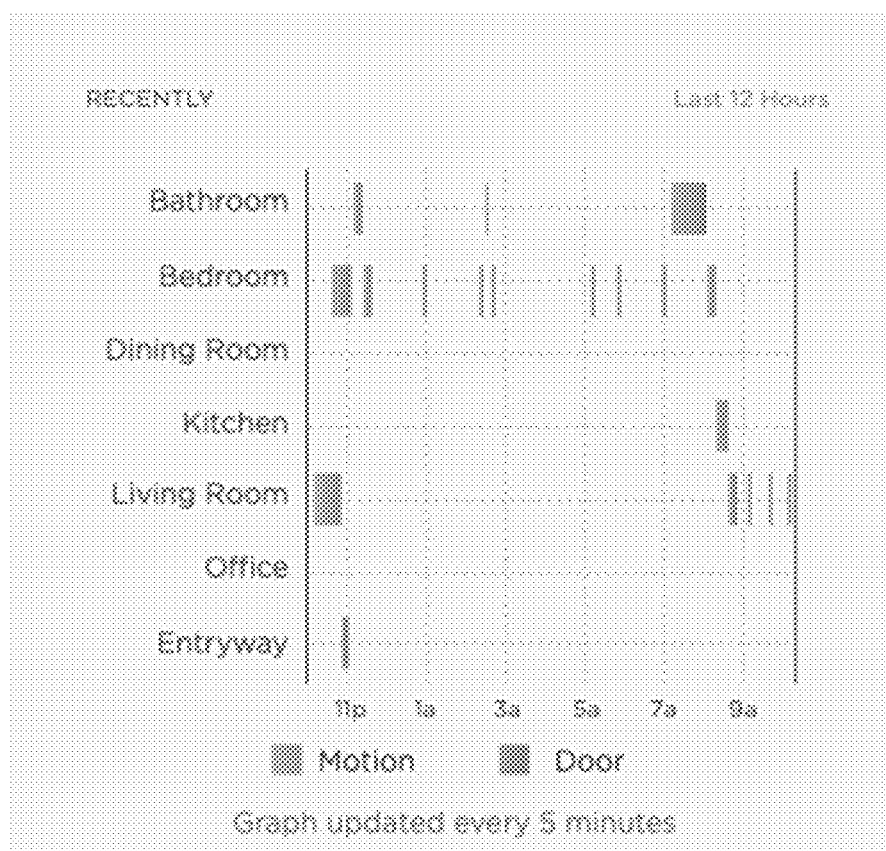
Figure 8E:
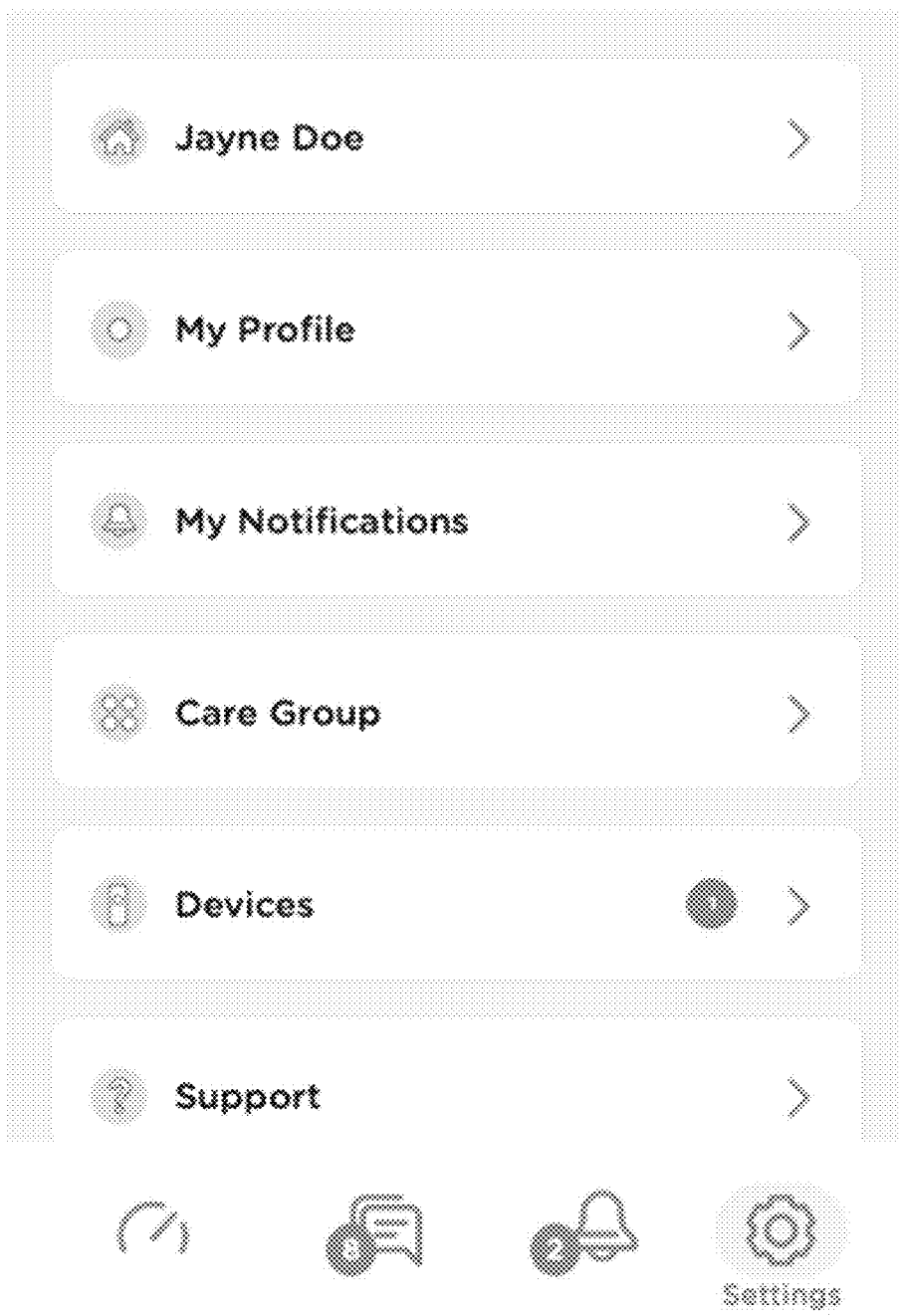
Figure 8F:
Figure 8F:
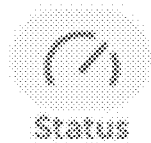
Figure 8F:
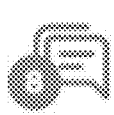
Figure 8F:
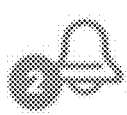
Figure 8F:
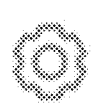
Figure 8G:
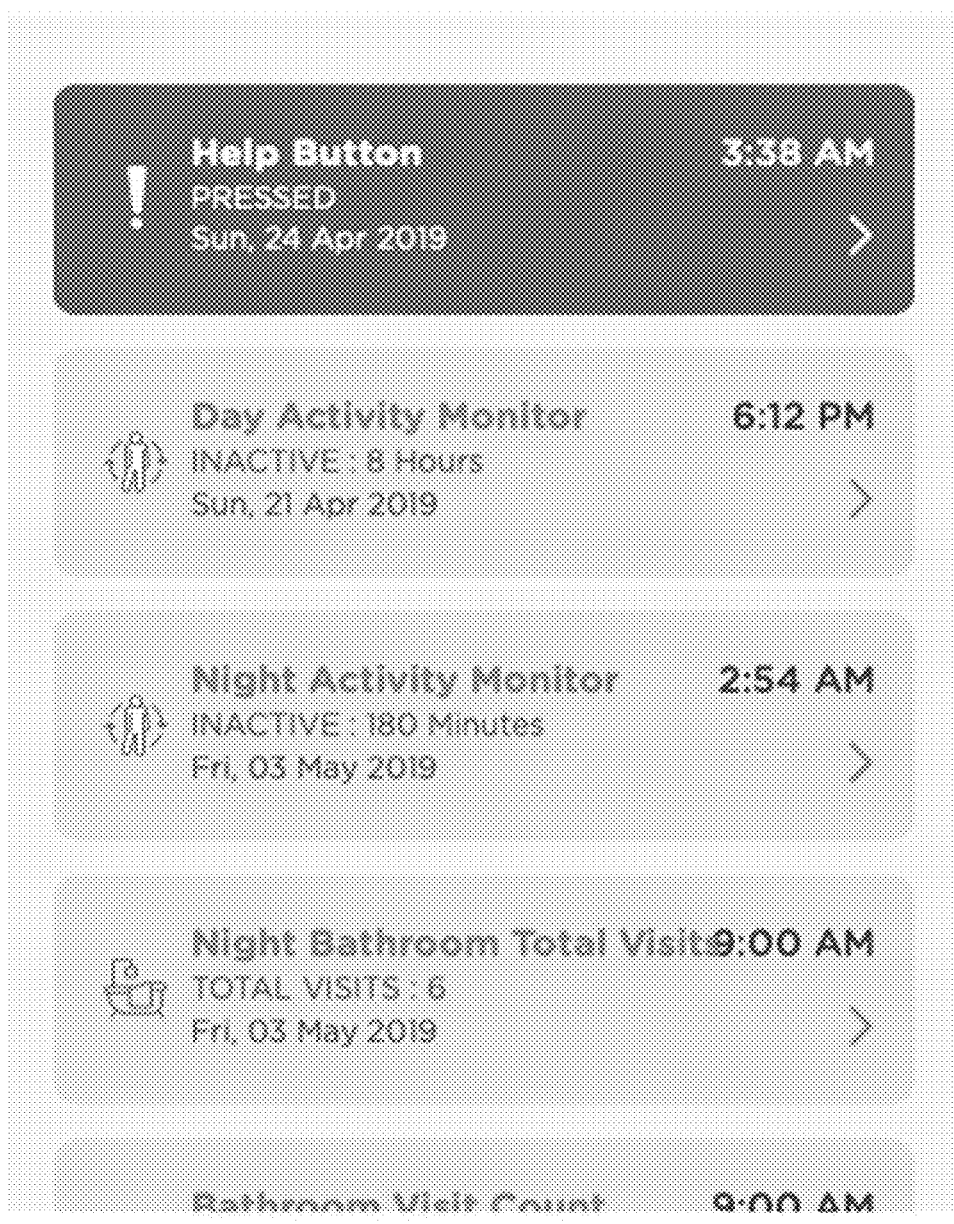
Figure 8H:
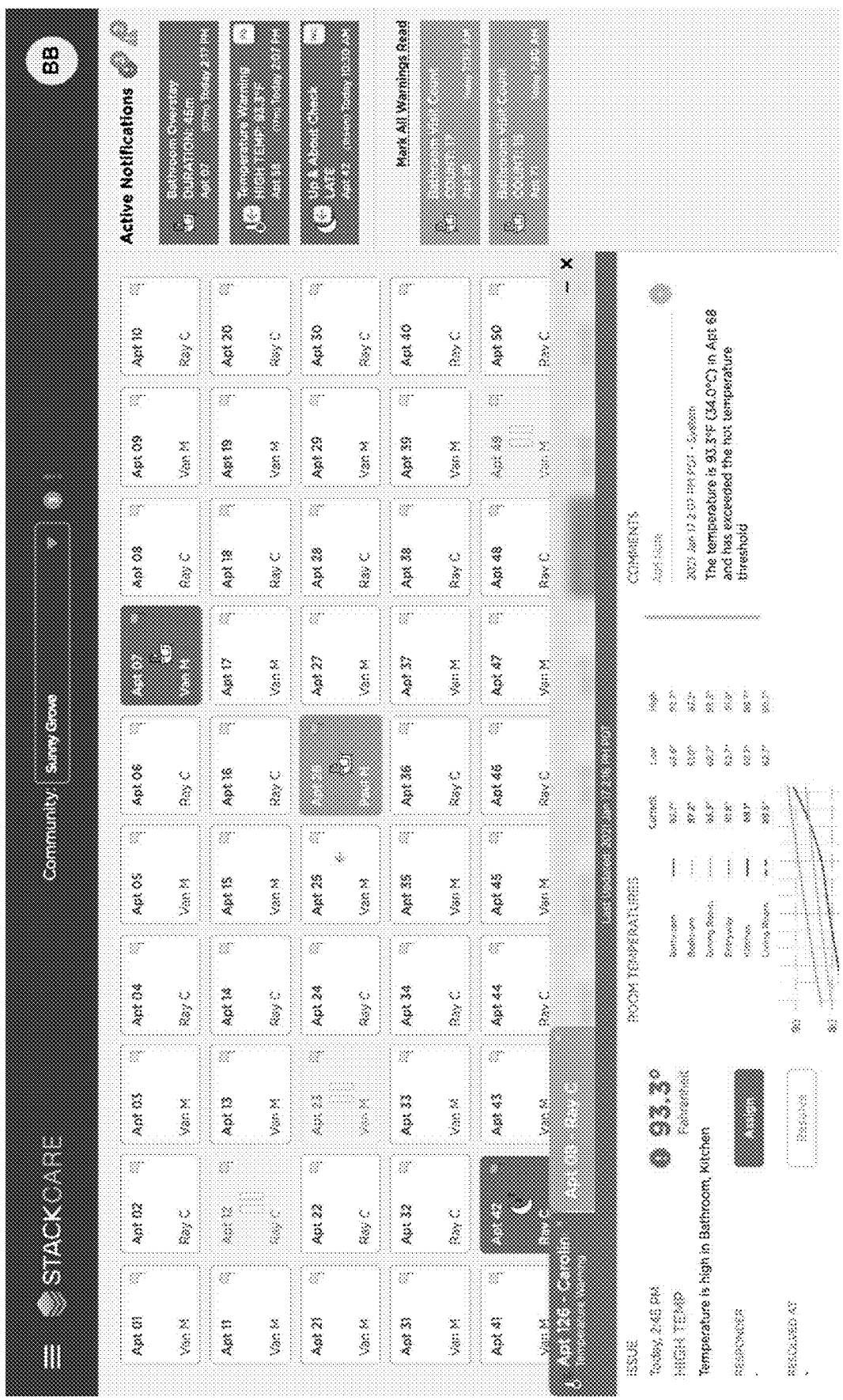
FIG. 8H shows an exemplary web client user interface.

Next, details on the Machine Learning to detect Sleep Duration & Quality are discussed. The system uses machine learning to analyze sleep duration and quality data collected from sensors to provide insights into the individual's sleep patterns. As shown in FIG. 6, the AI/machine learning algorithm is trained on a large dataset of sleep data to identify patterns and anomalies in sleep behavior. The algorithm takes into account various parameters such as the duration of sleep, the time taken to fall asleep, the number of times the individual wakes up during the night, and the time spent in each stage of sleep (REM, deep, light).

Based on this analysis, the system can provide insights into the individual's sleep quality and duration, and identify potential issues such as insomnia, sleep apnea, or other sleep disorders. This information can be shared with caregivers or family members to help them understand the individual's sleep patterns and take appropriate action if necessary.

Additionally, the system can provide recommendations to improve sleep quality and duration, such as adjusting the temperature or lighting in the bedroom, incorporating relaxation techniques or sleep hygiene practices, or seeking medical attention if necessary. In this manner, sleep data provides valuable insights into the individual's sleep patterns and can help caregivers and family members better understand the individual's needs and take appropriate action to ensure a good night's sleep.

In one embodiment, the AI Identifies Go-to-Bed time with Random Forest-Using identified sleep "features" and labeled data for training, develop a classification for choosing the best option for Go-to-Bed time. The system would first need to identify relevant "features" or variables from the sleep data that are most predictive of the optimal bedtime. This could include factors such as the time the individual wakes up in the morning, the duration and quality of sleep they typically get, and any other relevant factors such as their age, medical history, or lifestyle habits. Once these features have been identified, the system can use labeled data to train a Random Forest model to predict the best bedtime for the individual based on these factors. Labeled data could include information on when the individual typically goes to bed and wakes up, as well as any relevant factors that may impact their sleep patterns. The Random Forest model works by creating multiple decision trees, each of which independently evaluates the importance of different features in predicting the optimal bedtime. The model then combines the results from each tree to generate a final prediction. Once the Random Forest model has been trained, the system can use it to predict the optimal bedtime for the individual based on their sleep data. This information can be used to help the individual establish a consistent bedtime routine and improve the quality and duration of their sleep.

In another embodiment, the system calculates Duration w/Up & About time where machine learning is used to calculate the duration of an individual's sleep, taking into account any time they spend up and about during the night. The system would first identify relevant features from the sleep data that are most predictive of the duration of sleep, such as the time the individual goes to bed, the time they wake up, and any interruptions or periods of wakefulness during the night. Once these features have been identified, the system can use machine learning algorithms such as regression analysis to predict the duration of sleep based on these factors. This analysis could also take into account any time the individual spends up and about during the night, adjusting the duration of sleep accordingly. For example, if the individual spends 30 minutes up and about during the night, The system could subtract this time from the predicted duration of sleep to arrive at a more accurate estimate of how long the individual slept. Using machine learning to calculate the duration of an individual's sleep can provide valuable insights into their sleep patterns and help caregivers and family members better understand the individual's needs and take appropriate action to ensure they are getting enough rest.

In another embodiment, Sleep Quality is determined using motion levels (high, low, and no motion). The system can use machine learning to evaluate an individual's sleep quality based on their levels of motion during the night. Specifically, the system can use motion data from sensors in the individual's room to classify periods of high, low, or no motion during the night. Once these motion levels have been classified, the system can use machine learning algorithms such as classification models to predict the individual's sleep quality based on these factors. For example, a model could be trained to predict that periods of high motion are associated with lower sleep quality, while periods of low or no motion are associated with better sleep quality. The system collects labeled data from individuals about their sleep quality and corresponding levels of motion during the night. This data could be used to train and validate the models, allowing them to accurately predict sleep quality based on motion data. Once the models have been trained, the system can monitor an individual's sleep quality in real-time and provide notifications to caregivers or family members if sleep quality is significantly reduced. This can be especially valuable for elderly individuals who may be more prone to sleep disturbances and disruptions. By identifying periods of poor sleep quality early, caregivers and family members can take appropriate action to improve the individual's sleeping environment and overall well-being.

Next, an example of applying machine learning to bathroom visit count is detailed. FIG. 6 shows an exemplary process to determine unusual bathroom visitations as a check on wellness. The system performs the following operations:

"Rolling Window". Detecting outliers based on history
Continually updating for all users
Count only visits with possible toilet usage (i.e. not washing hands)-Minimum duration is calculated per user based on night-time usage
"Blurring" Visits-Getting ready in the morning-short activity outside of the bathroom A rolling window approach to detect outliers and unusual patterns in an individual's behavior based on their historical data. This approach involves continually updating a statistical model of the individual's behavior over time, allowing the system to detect changes and anomalies in their behavior. For example, the system could use a rolling window to monitor an individual's bathroom usage over time, identifying periods of unusual or excessive usage that could indicate a health issue or other problem. The system could also filter out visits that are unlikely to involve toilet usage, such as visits where the individual only washes their hands. In addition, the system could calculate a minimum duration for each individual's bathroom visits based on their typical night-time usage. This can help filter out short, non-toilet-related visits and improve the accuracy of the system's analysis. The system could use blurring techniques to smooth out short bursts of activity that occur outside of the bathroom, such as getting ready in the morning. This can help prevent these short bursts of activity from being incorrectly classified as bathroom visits, improving the accuracy of the system's analysis. With the foregoing, the system can accurately monitor an individual's behavior over time and detect patterns and anomalies that could indicate health issues or other problems. This can be especially valuable for elderly individuals who may be more prone to health issues and require more frequent monitoring and care.

The system can use various metrics to track an individual's bathroom usage over time and identify changes and anomalies in their behavior. Some potential metrics could include:

Category (Night/Day/Total)
Number of visits
Number of visits in history
Cumulative mean visits
Cumulative median visits
Lower IQR
Upper IQR
too_low_threshold
too_high_threshold
upper_threshold
too_low_outlier
too_high_outlier
individual_outlier
Chart: min, low2, low1, high1, high2, max Category (Night/Day/Total): This metric can help differentiate between bathroom visits that occur during the day versus those that occur at night, and can help identify any differences in behavior patterns during these different times.

Number of visits: This metric can help track the total number of bathroom visits an individual makes over a given time period, and can be useful for detecting changes in behavior or identifying potential health issues.

Number of visits in history: This metric can provide context by showing how an individual's current bathroom usage compares to their historical usage patterns.

Cumulative mean visits: This metric can help track the average number of bathroom visits an individual makes over time, and can be useful for identifying changes in behavior or identifying potential health issues.

Cumulative median visits: Similar to the mean visits metric, this metric can track the median number of bathroom visits an individual makes over time.

Lower IQR: This metric can help identify the lower boundary of an individual's typical bathroom usage, and can be useful for detecting outliers or changes in behavior.

Upper IQR: This metric can help identify the upper boundary of an individual's typical bathroom usage, and can be useful for detecting outliers or changes in behavior.

By tracking these metrics over time, the system can help identify changes and anomalies in an individual's behavior and provide early warning of potential health issues or other problems. This can be especially valuable for elderly individuals who may be more prone to health issues and require more frequent monitoring and care.

too_low_threshold: This metric can help identify the lower threshold for an individual's typical bathroom usage. Visits below this threshold may be considered too infrequent and could signal potential health issues or changes in behavior.

too_high_threshold: This metric can help identify the upper threshold for an individual's typical bathroom usage. Visits above this threshold may be considered too frequent and could also signal potential health issues or changes in behavior.

upper_threshold: This metric can help identify the maximum number of bathroom visits an individual is expected to make during a given time period based on their historical usage patterns. Visits above this threshold may be considered outliers and could signal potential health issues or changes in behavior.

too_low_outlier: This metric can help identify visits that are significantly below an individual's typical usage patterns and may be considered outliers. This could be useful for identifying potential health issues or changes in behavior.

too_high_outlier: This metric can help identify visits that are significantly above an individual's typical usage patterns and may be considered outliers. This could also be useful for identifying potential health issues or changes in behavior.

individual_outlier: This metric can help identify visits that are significantly different from an individual's historical usage patterns, and could be considered outliers for that individual. This could be useful for detecting changes in behavior or identifying potential health issues.

In addition to these metrics, the system could use a chart to visually represent an individual's bathroom usage over time, with the min, low2, low1, high1, high2, and max points plotted on the chart. This can help provide a quick snapshot of an individual's typical usage patterns and identify any outliers or changes in behavior.

The system can provide care notifications to users. In one embodiment, the following notifications are provided:

| Real-Time | Batch |
|---|---|
| Help Button Press | Bathroom Overstay |
| Temperature Warning | Bathroom Visit Count ("soft" - clusters) |
| Resident Exit | Activity Monitor - Day |
| Exterior Door | Activity Monitor - Night |
| Security | Activity Monitor - Kitchen |
| | Night Bathroom Overstay |
| | Night Bathroom Total Time |
| | Night Bathroom Total Visits |
| | Up & About Check |

FIGS. 7A-7M details exemplary notifications generated by the system.

The temperature warning notification is triggered when the temperature in a particular room or area exceeds a certain threshold. The threshold may vary depending on the time of day, season, and other factors. To implement this notification, temperature sensors can be installed in different areas of the house or facility, such as bedrooms, living rooms, and kitchens. These sensors can send temperature data to the backend services through the data pipeline using Kafka streams. The backend services can then analyze the data and determine if the temperature in any area has exceeded the threshold. If the temperature exceeds the threshold, a notification can be sent to the mobile app or web client, alerting the caregiver or family member of the situation. The notification can include information such as the temperature reading, the location of the sensor, and the time of the reading. The notification can also include instructions on how to mitigate the situation, such as opening windows or turning on air conditioning. Additionally, the notification can be escalated to a more urgent level if the temperature continues to rise or if there is no response from the caregiver or family member. In one embodiment:

Temperature Reports every 10-12 minutes
Humidity Reports every 10-12 minutes
Heat Index calculated with temp and current humidity
High temperatures above high temp threshold
Low temperatures below low temp threshold
2 temperatures exceeding threshold required to trigger (2 consecutive from 1 zone, or 1 each from 2 zones)

To ensure that caregivers and family members are aware of temperature and humidity changes in a timely manner, temperature and humidity sensors can be configured to send reports to the backend services every 10-12 minutes. These reports can be processed in real-time by the data pipeline using Kafka streams.

The backend services can use the temperature and humidity data to calculate the heat index, which takes into account both temperature and humidity levels. If the heat index exceeds a certain threshold, a notification can be triggered to alert the caregiver or family member of the situation.

In addition to the heat index, the backend services can also monitor high and low temperatures. If the temperature in a particular zone exceeds the high or low temperature threshold, a notification can be triggered. To avoid false alarms, the threshold can be set such that two consecutive temperature readings from the same zone or one temperature reading from two different zones must exceed the threshold.

The notification can include information such as the temperature reading, the location of the sensor, and the time of the reading. The notification can also include instructions on how to mitigate the situation, such as opening windows or turning on air conditioning. Additionally, the notification can be escalated to a more urgent level if the temperature continues to rise or if there is no response from the caregiver or family member.

Resident Exit Notification is detailed next. To ensure the safety of elderly residents, The system can also monitor resident exits and send notifications to caregivers and family members if a resident exits the home or designated area without authorization. This can be accomplished by installing contact sensors on exterior doors or using motion sensors in key areas to detect when a resident leaves the home or designated area. The sensor data can be processed in real-time by the data pipeline using Kafka streams. If a resident exits the home or designated area without authorization, a notification can be triggered. The notification can include information such as the resident's name, the location of the sensor, and the time of the event. The notification can also include instructions on how to locate the resident and bring them back safely. To avoid false alarms, the system can be configured with a delay that allows the resident to return within a certain period of time without triggering a notification. Additionally, the system can be configured to ignore authorized exits, such as when a caregiver or family member accompanies the resident outside. In one embodiment:

Triggers on receipt of Contact Event true during window
Zone must have motion prior to door open (night checks may cause false positives)
1st check: No motion 30s after door close, send notification
2nd check: Motion seen 120s after door open, send follow-up The Resident Exit Notification is designed to trigger when a contact event is received within a specified time window. The notification is sent only if there is motion detected prior to the door opening, as this reduces the chances of false positives from night checks.

The notification process has two checks:
First check: If there is no motion detected for 30 seconds after the door is closed, a notification is sent.
Second check: If there is motion detected within 120 seconds of the door being opened, a follow-up notification is sent.

These checks help to ensure that the notification is only sent when there is a genuine exit event, and that the follow-up notification is only sent if the resident has not returned within a reasonable timeframe.

The Help Button Press Notification is described next. The Help Button Press Notification is triggered when a resident presses the help button. The notification is sent immediately, within 20 seconds of the button press. Once the notification is triggered, a caregiver or staff member is alerted to respond to the resident's call for assistance. The notification can be sent to a designated person or group, such as a nurse or security team, depending on the setup of the monitoring system. As the help button press may indicate an emergency situation, the 20-second time frame ensures that the notification is received in a timely manner, allowing the caregiver or staff member to respond promptly to the resident's needs. In one embodiment, the system requires button of type 'help' that triggers on receipt of true event (button press) during window.

When a help button of type help is pressed, the system triggers a notification. The notification can be sent to designated caregivers or emergency services. The notification can include information about the location of the help button and the identity of the resident who pressed the button. In addition, the notification can be accompanied by an audible alarm or other alert to draw attention to the situation. Once the notification has been triggered, caregivers or emergency services can respond promptly to the resident's needs.

The Security Notification Triggers when two motion events received within 20 minutes while unit is paused and activity in notification updated every 60s so user can see activity *after* notification triggered The Security Notification triggers when two motion events are received within 20 minutes while the unit is paused, indicating potential unauthorized entry. The notification includes activity updates every 60 seconds to keep the user informed of any additional activity after the notification was triggered.

The Exterior Door Notification Requires contact sensor type of 'exterior_door' and in one embodiment:
    Triggers on receipt of Contact Event true (door open) during window The exterior door notification requires a contact sensor type of exterior_door. It triggers on receipt of Contact Event true (door open) during the designated window.

Figure 9:
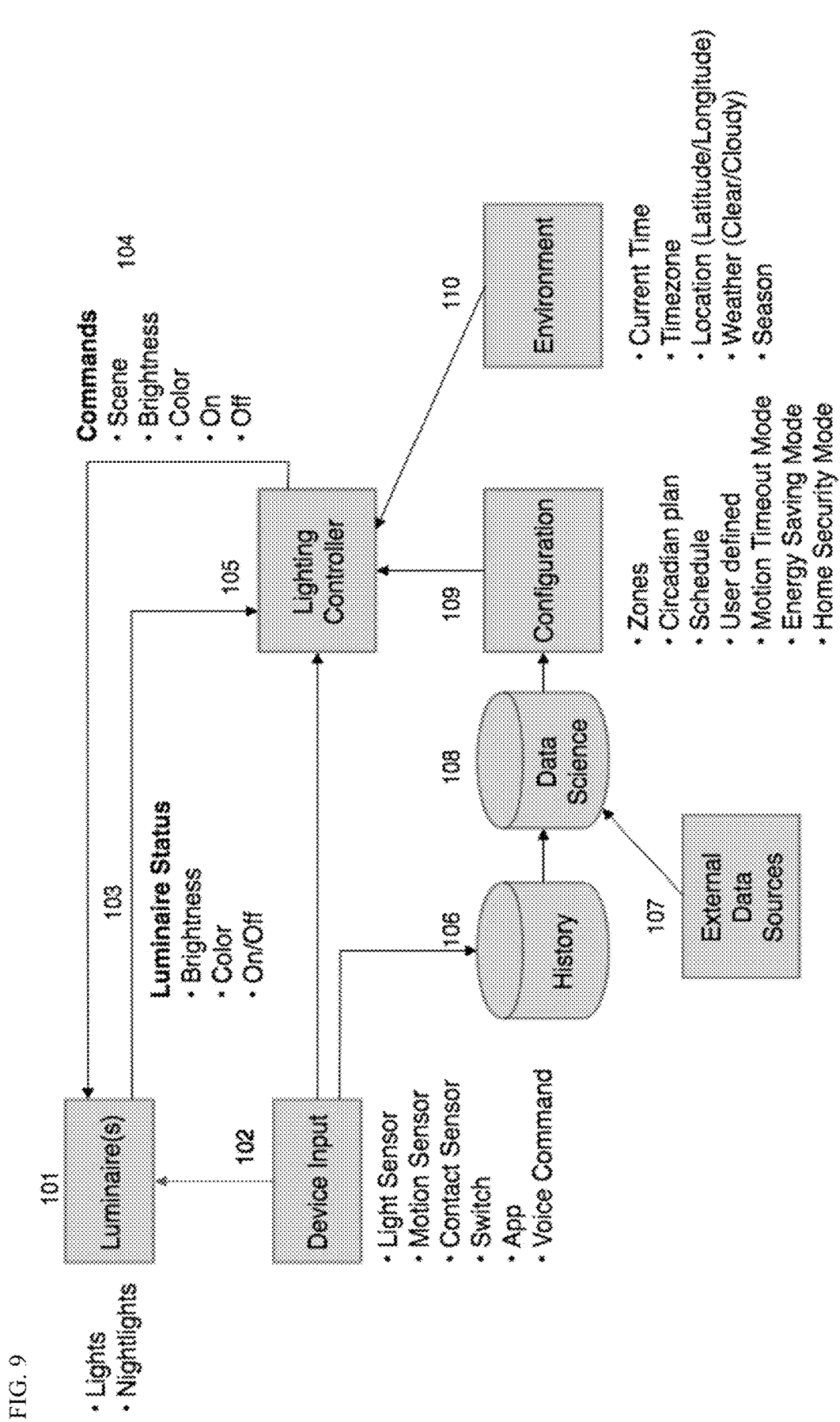
FIG. 9 shows an exemplary autonomous circadian lighting system with environmental monitoring and sensor input.
Figure 10:
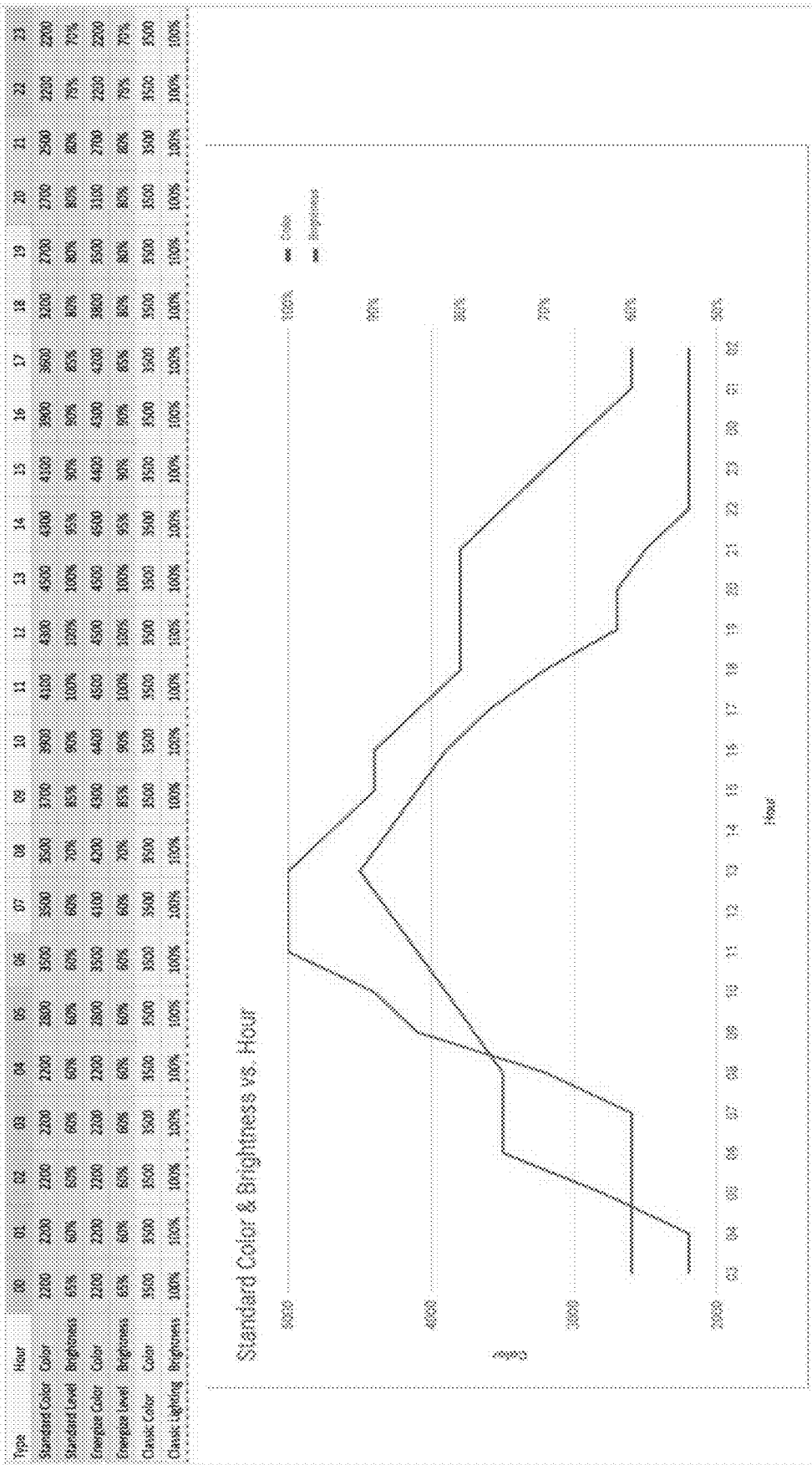
FIG. 10 shows an exemplary circadian lighting plan.

Next, batch notifications are detailed. In one embodiment, the following batch notifications are done:
    Daily Update
        Sent every day at 10: 30 am local time to all users
        Summarizes
        Sleep Data
        Bathroom Data
        Awareness of Recent Notifications
    Bathroom Overstay
        Configurables: duration (default: 60 mins)
        Uses Zone Occupancy data
        Triggers when ZO is established in bathroom and remains for <duration>
        Does not require continuous motion
        Only cleared if occupancy is established elsewhere
    Day Activity Monitor
        Configurables: duration (default: 8 hours)
        Uses Zone Activity data
        Triggers when there's been no activity in any zone for <duration>
    Night Activity Monitor
        Configurables: duration (default: 3 hours)
        Uses Zone Motion Activity data
        Triggers when there's been no activity in bedroom zone for <duration>
        Motion in non-bedroom zones does not clear
    Kitchen Activity Monitor
        Configurables: None
        Uses Zone Occupancy data
        Triggers when there's been two consecutive meals "missed"
        Requires at least 3 minutes of activity total during meals window (e.g. breakfast and lunch times)
    Night Bathroom Overstay
        Configurables: duration (default: 15 minutes)
        Uses Zone Occupancy data
        Window: 12 am-5 am
        Triggers when bathroom occupancy has exceeded <duration>
        Inhibits itself until visit is over
    Night Bathroom Total Visits
        Configurables: count (default: 5)
        Uses Zone Occupancy data
        Window: 12 am-5 am
        Triggers when bathroom visits have exceeded <count>
        Inhibits itself until next day
    Up & About Check
        Configurables: local_time_start, local_time_end
        Uses Zone Motion Activity data
        Triggers when insufficient non-bedroom activity has been detected by <local_time_end>
        Inhibits itself until next day
    Bathroom Visit Count—Soft
        Configurables: none
        Uses Bathroom Visit Features
        Predictive Analytics
        Triggers when a cluster of outliers is detected
        3-4 outliers in 7 days FIG. 9 shows an exemplary autonomous circadian lighting system with environmental monitoring and sensor input while FIG. 10 shows an exemplary circadian lighting plan. This solution monitors numerous environmental factors and sensor input to provide additional context for an appropriate Lighting setting at any particular moment. The system includes light sources 101 controlled by various inputs 102 such as data from the light sensor, motion sensor, contact sensor, switch, app, or voice command. The light sources 101 is also controlled by a lighting controller 105. Device input 102 is stored in history database 106 which is provided to a data science database 108 that also receives external data sources 107. The data science database is used to set configuration 109 which controls the lighting controller 105. Configuration 109 includes data on zones, circadian plan, schedule, user preference, motion timeout mode, energy saving mode, and home security mode. The lighting controller 105 also receives input from environment 110 such as time, time zone, location, weather, and season, for example.

Next, a Circadian Lighting Plan is detailed. A circadian lighting plan is a type of lighting system that is designed to mimic the natural pattern of daylight, which helps to regulate the body's internal clock or circadian rhythm. This type of lighting system is particularly important in environments where people spend a lot of time indoors and are not exposed to natural sunlight.

The circadian lighting plan involves changing the color and intensity of the lighting throughout the day to mimic the natural pattern of daylight. The lighting system is typically set up to be brighter and bluer in the morning to help promote wakefulness and alertness. In the afternoon, the lighting becomes warmer and less intense to help promote relaxation and prepare the body for sleep. The circadian lighting plan can be adjusted based on the specific needs of the space and the people using it. For example, in a healthcare setting, the lighting system may be designed to promote healing and reduce stress in patients. In a workplace setting, the lighting system may be designed to improve productivity and reduce fatigue.

Implementing a circadian lighting plan requires a combination of hardware and software components. Specialized LED lighting fixtures, sensors, and controls are used to create the desired lighting effects. Software programs can be used to monitor and adjust the lighting system based on the time of day and the needs of the users.

Overall, a circadian lighting plan can provide a range of benefits, including improved mood, increased productivity, and better sleep quality. It is an important consideration for any space where people spend a significant amount of time indoors. Numerous environmental factors and sensor input to provide additional context for an appropriate Lighting setting at any particular moment. Circadian lighting plans aim to provide lighting that is optimized for the user's health and wellbeing based on a variety of factors, including the time of day, natural light levels, and the user's activities and needs. Sensors can be used to monitor these factors and provide additional information that can help inform the lighting plan, such as the user's location within the home, their movement patterns, and the presence of natural light sources. By combining this data with an understanding of the user's circadian rhythm and the effects of light on the body, a circadian lighting plan can adjust the color and intensity of the lighting to promote better sleep, mood, and overall health.

What is claimed is:

1. A method for encouraging physical activity among one or more subjects, comprising:
   using sensors to track motion and other physical activity of the subject;
   creating an activity index based on the tracked data to measure overall activity levels; and
   providing feedback to the senior through a chatbot or other interface to encourage physical activity and suggest changes to their routines.

2. The method of claim 1, comprising managing cognitive decline by:
   tracking daily routines and patterns using sensors and deep learning of the daily routines and patterns;
   using predictive analytics to forecast the rate of cognitive decline;
   providing feedback to the user on how to change their patterns based on the predictive analytics and encouraging variance in daily routines to slow cognitive decline.

3. The method of claim 1, comprising:
   capturing streaming data from one or more sensors;
   applying one or more deep learning models to identify one or more activities of the person;
   applying one or more directed acyclic graphs (DAGs) to the streaming data and the one or more activities of the person to identify a pattern from the streaming data for alert or notification of one or more predefined conditions affecting wellness.

4. The method of claim 1, comprising monitoring a humidity sensor for measuring ambient humidity, analyzing the humidity data and generating alerts based on predefined humidity thresholds.

5. The method of claim 1, comprising notifying caregivers of relevant events, including the steps of setting inhibitions based on time since last event, implementing related events such as bathroom overstays, and using machine learning to determine sleep duration and quality.

6. The method of claim 1, comprising identifying a sleep time, including the steps of training a random forest model using identified sleep features and labeled data, and developing a classification algorithm for determining said sleep time.

7. The method of claim 1, comprising calculating sleep quality using motion levels, including the steps of analyzing high, low, and no motion data, and using said analysis to determine sleep quality.

8. The method of claim 1, comprising analyzing motion data, identifying periods of wakefulness, and determining sleep duration based on said data.

9. The method of claim 1, comprising detecting outliers in bathroom visit data, including the steps of continually updating said data for all users, counting only visits with possible toilet usage, and calculating a minimum duration per user based on night-time usage.

10. The method of claim 1, comprising measuring temperature and humidity levels, including the steps of collecting temperature and humidity reports every 10-12 minutes, and calculating heat index based on said data.

11. The method of claim 1, comprising triggering temperature warning notifications, including the steps of setting high and low temperature thresholds, requiring two consecutive temperatures above or below said thresholds to trigger a notification, and sending said notification to relevant caregivers.

12. The method of claim 1, comprising triggering exit notifications, including the steps of requiring motion in a zone prior to door open, checking for motion 30 seconds after door close, and sending a notification if no motion is detected, and checking for motion 120 seconds after door open and sending a follow-up notification if said motion is detected.

13. The method of claim 1, comprising monitoring a user environment with a plurality of sensors for measuring environmental factors; and analyzing the measured data and generating alerts based on predefined criteria.

14. The method of claim 1, comprising detecting user motion with a motion sensor for detecting movement within a designated area; and analyzing the motion data and generating notifications based on predefined criteria.

15. The method of claim 1, comprising monitoring an environment temperature with a temperature sensor for measuring ambient temperature; and analyzing the temperature data and generating alerts based on predefined temperature thresholds.

16. The method of claim 1, comprising monitoring sleep with a motion sensor for detecting body movement during sleep; and analyzing the motion data and calculating sleep duration and quality metrics.

17. The method of claim 1, comprising controlling a lighting system with a plurality of sensors for measuring environmental factors; and generating lighting plans based on the measured data and predefined criteria.

18. The method of claim 1, comprising monitoring an exit with a contact sensor for detecting the opening and closing of an exterior door or a motion sensor for detecting movement within a designated area; and generating notifications based on predefined criteria.

19. The method of claim 1, comprising monitoring a request from a help button for triggering an alert when pressed and generating notifications based on the alert.

20. The method of claim 1, comprising monitoring a plurality of motion sensors for detecting movement within one or more designated areas and analyzing the motion data and generating notifications based on predefined criteria.

* * * * *